US012607759B2

(12) United States Patent
Barberá Ballester et al.

(10) Patent No.: US 12,607,759 B2
(45) Date of Patent: Apr. 21, 2026

(54) READOUT NETWORK TOPOLOGY FOR POSITRON EMISSION TOMOGRAPHY DEVICES WITH TIME-OF-FLIGHT

(71) Applicants: General Equipment for Medical Imaging, S.A., València (ES); Consejo Superior de Investigaciones Científicas (CSIC), Madrid (ES); Universitat Politècnica de València, València (ES)

(72) Inventors: Julio Barberá Ballester, València (ES); Antonio Javier González Martínez, València (ES); José María Benlloch Baviera, València (ES); Noriel Pavón Hernández, València (ES)

(73) Assignees: General Equipment for Medical Imaging, S.A., València (ES); Consejo Superior de Investigaciones Cientificas (CSIC), Madrid (ES); Universitat Politécnica de València, València (ES)

(*) Notice: Subject to any disclaimer, the term of this patent is extended or adjusted under 35 U.S.C. 154(b) by 211 days.

(21) Appl. No.: 18/632,998

(22) Filed: Apr. 11, 2024

(65) Prior Publication Data

US 2024/0255660 A1     Aug. 1, 2024

Related U.S. Application Data

(63) Continuation of application No. PCT/ES2022/070643, filed on Oct. 11, 2022.

(30) Foreign Application Priority Data

Oct. 12, 2021     (ES) ............................... ES202130959

(51) Int. Cl.
    *G01T 1/29*          (2006.01)
    *A61B 6/03*          (2006.01)
    (Continued)

(52) U.S. Cl.
    CPC ............ *G01T 1/2985* (2013.01); *A61B 6/037* (2013.01); *A61B 6/4233* (2013.01); *G01T 1/247* (2013.01)

(58) Field of Classification Search
    CPC ....... G01T 1/2985; G01T 1/247; A61B 6/037; A61B 6/4233
    See application file for complete search history.

(56) References Cited

U.S. PATENT DOCUMENTS

| 7,476,864 | B2 | 1/2009 | Benlloch Baviera et al. |
| 2016/0327657 | A1 | 11/2016 | Zhang et al. |

(Continued)

FOREIGN PATENT DOCUMENTS

| EP | 3399345 | A1 | 11/2018 |
| WO | 2019228944 | A1 | 12/2019 |

OTHER PUBLICATIONS

Extended European Search Report and Written Opinion issued in application No. 22880461.3 on Sep. 18, 2025 (4 pages).

(Continued)

*Primary Examiner* — Hugh Maupin

(74) *Attorney, Agent, or Firm* — Boyle Fredrickson, S.C.

(57) ABSTRACT

An electronic readout network topology for positron emission tomography is able to provide Time of Flight for photodetectors arranged in matrix arrays made up of a plurality of silicon photomultipliers. Each photodetector has anode and cathode terminals. The readout network topology ensures suitable polarisation of the set of photodetectors and provides a reduction diagram by creating a single connection to extract a unique time reference signal that is accurate and (Continued)

synched up in phase to a detection event at any position of the photodetector matrix instead of connecting to each individual photodetector. A fast amplifier with low input impedance is electrically coupled to this time reference signal, creating a path of low impedance for the rapid transition signals, reducing the total parasitic capacitance of the parallel arrangement of detectors, and improving the time response of the detector block. Moreover, the readout electronics creates a smaller number of positioning signals.

21 Claims, 14 Drawing Sheets

(51) Int. Cl.
*A61B 6/42* (2024.01)
*G01T 1/24* (2006.01)

(56) References Cited

U.S. PATENT DOCUMENTS

| 2018/0372822 | A1 | 12/2018 | Kim et al. |
| 2020/0041665 | A1 | 2/2020 | Mintzer et al. |
| 2021/0199823 | A1 | 7/2021 | Li et al. |
| 2021/0223414 | A1* | 7/2021 | Harmon .............. G01T 1/20185 |

OTHER PUBLICATIONS

González, et al., "A PET Design based on SiPM and Monolithic LYSO Crystals: Performance Evaluation", IEEE Transactions on Nuclear Science, Jan. 10, 2016, vol. 63, No. 5, (pp. 2471-2477).

\* cited by examiner

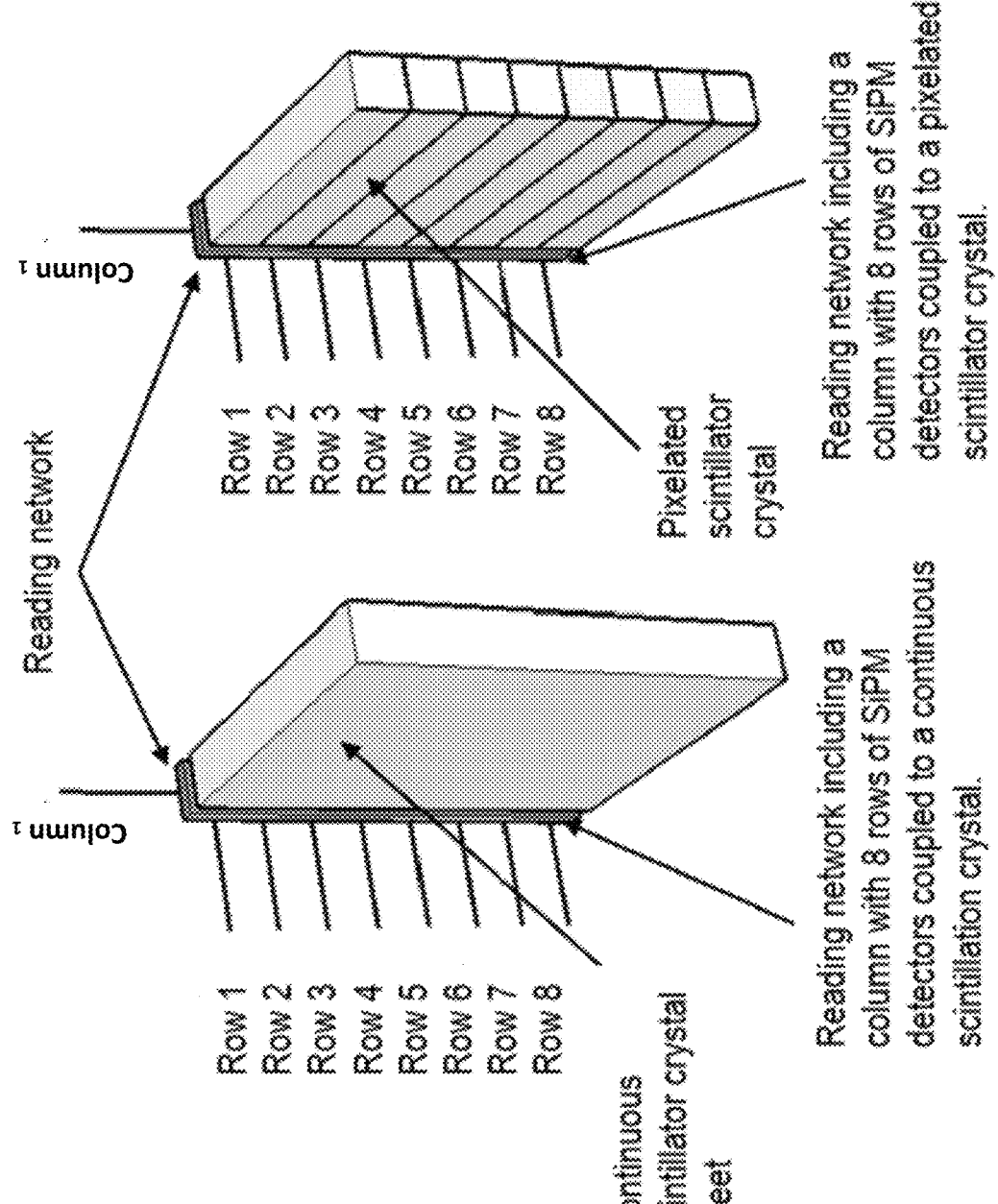

Column 1

Reading network

Row 1
Row 2
Row 3
Row 4
Row 5
Row 6
Row 7
Row 8

Pixelated scintillator crystal

Reading network including a column with 8 rows of SiPM detectors coupled to a pixelated scintillator crystal.

Column 1

Row 1
Row 2
Row 3
Row 4
Row 5
Row 6
Row 7
Row 8

Continuous scintillator crystal sheet

Reading network including a column with 8 rows of SiPM detectors coupled to a continuous scintillation crystal.

Figure 13

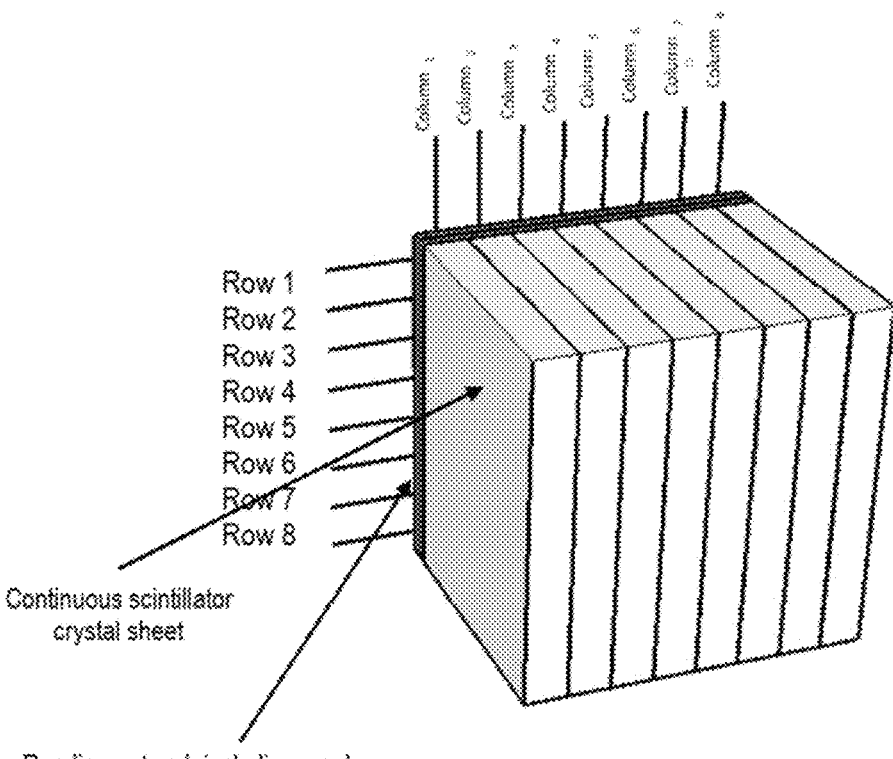
Continuous scintillator
crystal sheet
Reading network including a column
with 8 rows of SiPM detectors coupled
to a continuous scintillation crystal.
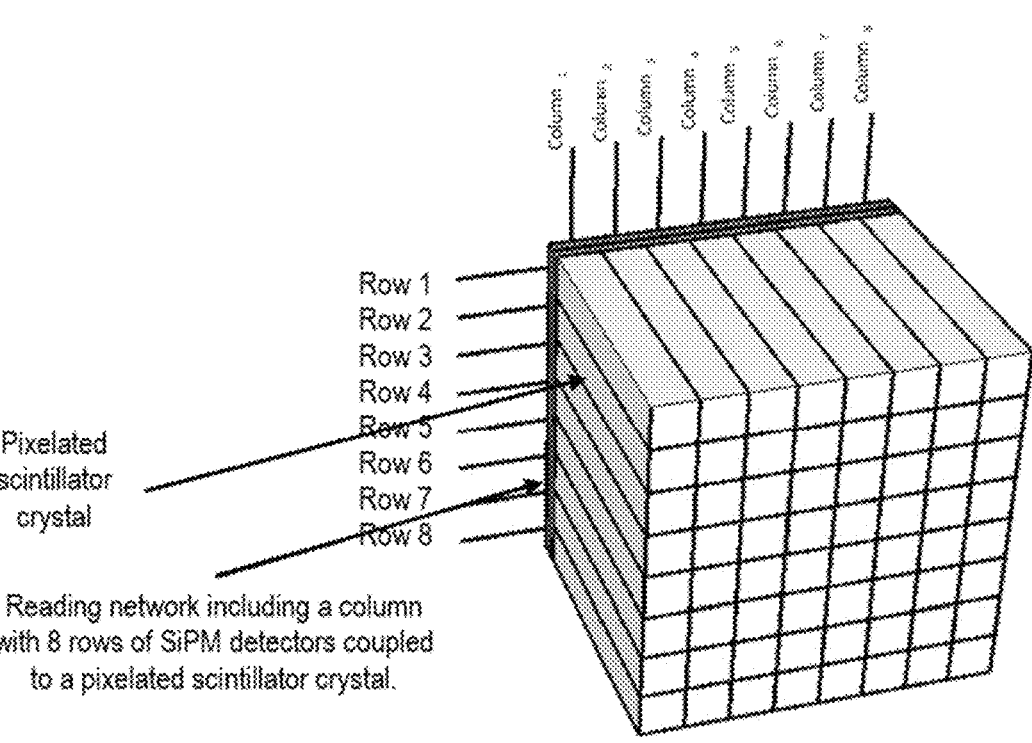
Pixelated
scintillator
crystal
Reading network including a column
with 8 rows of SiPM detectors coupled
to a pixelated scintillator crystal.
Figure 14

READOUT NETWORK TOPOLOGY FOR POSITRON EMISSION TOMOGRAPHY DEVICES WITH TIME-OF-FLIGHT

CROSS-REFERENCE TO RELATED APPLICATIONS

This application is a continuation of and claims priority to PCT Application No. PCT/ES2022/070643, filed Oct. 11, 2022, which, in turn, claims priority to Spanish Application No. P202130959, filed Oct. 12, 2021, the entire contents of each application is incorporated herein by reference.

FIELD OF THE INVENTION

The present invention belongs to the field of medical devices for nuclear imaging. This kind of electronic design topology is intended to be a generic use in detectors for nuclear imaging, particularly in silicon photomultiplier individual photodetectors for Time-of-Flight applications.

BACKGROUND OF THE INVENTION

Positron Emission Tomography (PET) involves administering living beings with trace amounts of biomolecules labelled with a positron-emitting radionuclide (radiotracers) and subsequent detection of the pairs of high energy gamma photons produced simultaneously following each positron-electron annihilation within the tissue.

The generated high energy photon pairs move in opposite directions, following straight lines, called Lines of Response (LOR), so that, it is possible to infer these LORs by detecting both photons' coordinates using gamma detectors surrounding the observed tissue. We also know that only the segment of the line that covers the space between the two gamma ray detectors touched by the pair of photons has a real probability to contain the point on the tissue where the positron-electron annihilation occurred.

So far, we have a collection of line segments containing information that allows us to infer radiotracer distribution within the tissue, using software reconstruction methods. This is what all PET technology usually does.

All PET systems include a timing coincidence filter to discriminate photons that are not clearly related to the same annihilation event, but the resolution of this timing filter (usually from a few ns to a few tens of ns) is not enough to extract more information. It is because in this time the light can travel a distance larger than the trans-axial dimension of the system.

Advanced PET systems called Time-of-Flight PET system (TOF-PET), are capable of measuring the time interval between the arrival of both high energy photons to their corresponding detectors with a high resolution (ranging from a few tens of picoseconds to a few hundreds of picoseconds), allowing to establish a specific short segment on the LOR (only a few cm) that has a real probability to contain the point on the tissue where the positron-electron annihilation occurred. The result is not a point on the LOR, but a segment, due to the uncertainty of the time measurement, characterized by the timing resolution of the system. In this case, the size of the data blocks required for the reconstruction process is considerably lower, what reduces the processing time, the proportion of invalid data and increases the precision and quality of the images. So, the accuracy of the measurement of the time arrival difference between both gamma rays involved in a single positron-electron annihilation is key to improve the next generation of Time-of-Flight PET detectors.

Another field of improvement is related to the gamma ray imaging detector technology, based on a detector tandem made of a scintillator detector coupled to a planar photodetector block made of a matrix arrangement of individual photodetectors.

In the text that follows (unless otherwise specified) we will use the word "photodetector" as well as "photodetector block" or "photodetector arrangement", to refer to a block that includes a plurality of individual photodetectors in a matrix arrangement, while, when referring to a photodetector formed by a single detector (for example an individual SiPM), we will explicitly indicate that it is an individual photodetector.

Nowadays, the older photodetector technology, based on photomultiplier tubes (PMT), is being substituted by advanced individual photodetectors based on solid state devices (for example SiPM) arranged in a matrix of (p×q) individual photodetectors. This allows to drastically reduce the cost per unit of photodetector area, but also important improvements in individual photodetectors reliability, uniformity, weight, electromagnetic immunity, etc. Arrangements of 4×4, 8×8, 16×16, 8×1, 16×1 SiPM, can usually be found in papers and are offered by manufacturers.

The drawback of this type of individual photodetectors is their high terminal capacitance which, together with their internal resistance, limits their response time. This is even worse if a large number of individual photodetectors are put together sharing the same connection points (parallel connection) since in this case, the total terminal capacitance is the sum of the individual capacitances of the individual photodetectors, provoking a worse time resolution of the system. So, regarding SiPMs based photodetectors, it is not possible to reduce the number of signals to process using the well-known reduction readout schemes trusted for the PMT photodetectors.

Therefore, to obtain the positioning and timing signals for the newest ToF-PET systems, the readout circuits usually deal with all SiPM signals separately at hardware level, and then, all these signals are digitized, generating a big amount of data to be later processed. It is very difficult to deal with the large number of components and circuits required if each SiPM should be acquired separately for energy and time response. If the time response is obtained after analog processing of the separated SiPM outputs, the time resolution is worsened unless very careful design be carried out across the whole analog design, to fine tune and equalize all the signal paths. This will result in an almost unattainable design if only a very small space is available. This is especially important if discrete electronics is used, although integrated electronics can benefit too from this arrangement. That is why, the creation of new reducing schemes become very useful to go forward with the possibility that new ToF-PET systems take advantages of the new SiPM photodetectors.

In order to reduce the effective capacitance of the individual photodetectors, for example SiPM, and its drawbacks, some authors used specific readout electronics to deal with it. US 2016/0327657 A1 describes a readout system that reduce the individual photodetector capacitance by a factor, coupling the individual SiPM photodetector to an analog front-end electronic through a transformer in a differential bootstrapping configuration. This could generally be achieved by connecting the individual photodetectors to any front-end electronics with a very low input impedance, not just by a transformer. Further, using transformers greatly complicates the possibility of miniaturization required for photodetectors blocks with many individual photodetectors such as those in the aforementioned arrangements.

They also split each individual photodetector signal by frequency band in order to use the high frequencies for timing purposes and the lower frequencies for energy and position determination, but they do not propose any reduction in the number of signals required, nor do they identify it as an issue to address, and even less do they disclose any scheme to achieve it.

Regarding the charge signals coming from each detector cell there are a lot of reduction schemes from the PMT era that are suitable for the SiPM arrangements era, provided that a few required modifications are made to avoid the drawback of the parallel addition of all SiPM capacitances, as we do in the present invention. Some examples of these reduction schemes can be found in our previous patents (U.S. Pat. No. 7,476,864B2, Pub. US20190004188A1). These are reduced to the specific scope of PET without ToF.

BRIEF DESCRIPTION OF THE INVENTION

In the present specification, whenever there is a reference to SiPMs as the most usual photodetectors, it should not be interpreted as a limitation of the invention to this type of photodetectors.

In an ideal PET made out of multiple detector modules, including at least one photodetector block per module it is required to obtain, with a sufficiently high precision some variables, such as the identification of the specific blocks receiving the annihilation photons interactions, the position in X and Y on the photodetector blocks surface, the Depth-of-Interaction within the scintillator detector volume, and the timestamps of such impact. The precision to obtain these variables depends on many characteristics related to the selected scintillator crystal type and geometry, the photodetector configuration and the associated electronics.

Due to the manufacturing process of photodetectors, such as SiPM, some spreading is found in different specific characteristics of the parts produced, even in a same batch, such as breakdown voltage, gain, time response, etc. In order to obtain the best uniformity, linearity and time accuracy all over the individual photodetectors surface, the circuits coupled to the individual photodetectors should deal with each of these deviations.

A readout electronic topology is provided in a variety of embodiments, as a signal reduction scheme, allowing the connection of a full arrangement of advanced individual photodetectors, such as of the individual SiPM photodetector type, containing a defined number of rows and columns, resulting in a single output, defined as a common timing signal used as the reference in the Time-of-Flight measurement of the entire photodetector block (simply called, the photodetector), maintaining the high time resolution required for ToF-PET systems. This represents a remarkable advance in reduction schemes of signals coming from a ToF-PET photodetector, to be processed and digitized, while ensuring a high image quality and a high performance of other measured parameters.

At the same time this arrangement allows to obtain individual uncoupled signals from each individual photodetector, and feeding those uncoupled signals to other suitable readout networks that collect all the charges of the photodetector arrangement, to accurately determine the event position and energy, without altering the high frequency components of the fast signals required for the determination of time references used in time-of-flight measurement.

These uncoupled output charge signals are compatible with other state of the art readout electronic circuits commonly used to reduce the number of charge signals, from (p×q) signals to (p+q) signals, and others, maintaining the capability to measure the event energy and position.

All the routes from each individual photodetector terminal to the circuit point where the single common timing signal is obtained, are tuned to synchronize the starting edges of all individual timing signal coming from any individual photodetector.

When a scintillation light pulse reaches the first, among any of the individual photodetectors, such as a SiPM, the starting edge of the highest frequency component of the signal generated passes through a very high-frequency band-pass filter formed by the active individual photodetector, a bias filter and an amplifier used to boost the timing output signal. The filter frequency band is close to the highest frequency components of the photodetector pulse.

A parallel set of different filters (charge filters) with a significant lower frequency band (a frequency at least 10 times lower than previous one) is used to connect the photodetector signals apart, to another readout network designed to extract the charges involved in the events at any place inside the photodetector.

The signals of both filters do not interfere each other due to its frequency separation, allowing us to have both, an early accurate single timing signal of an event occurred at the position of any individual photodetector in the arrangement, and the belated charge signals generated at each one of the individual photodetectors.

The present invention has a first object a readout network topology for positron emission tomography (PET) with time of flight (TOF) capabilities to extract position and time information in the area of gamma-ray detection comprising:

a plurality of individual photodetectors arranged in p×q matrix configuration on an electronic Printed Circuit Board (PCB) to conform a photodetector capable to process the light arriving to the matrix area and providing information to determine spatial coordinates and timing signal, each individual photodetector having an anodic terminal and a cathodic terminal, a connection of all similar terminals of one of the two types of photodetector terminals (either the anodic ones or the cathodic ones) to a Single Junction at the PCB, which further splits into two routes, the first one of these routes connects the Single Junction, by means of a specific impedance, to the proper source polarity, wherein "proper polarity" means: Vbias if the wired terminals to the Single Junction are the cathodes or GND if the wired terminals to the Single Junction are the anodes, wherein the specific impedance, either Za (if the wired terminals are the anodes) or Zk (if the wired terminals are the cathodes), is working as part of the photodetector bias circuit, and its resistance is set to be less than 10% compared to the resistance of the rest of the route from the Single Junction to GND and, the second one of these routes feeds the unified signal created at the Single Junction, into a fast amplifier, in order to obtain a single timing signal regarding the whole photodetector, no matter which specific individual photodetector it comes from, an individual connection of all the photodetector terminals, different from those ones connected to the Single Junction, by means of two separate filtering circuits for each photodetector terminal, the first filtering circuits named bias filters (TBF or BBF), complete the bias circuits for all individual photodetectors, connecting, by means of them, the individual photodetector terminals to the proper source polarity, wherein "proper" means that it is Vbias if the photodetector terminal is the cathode or GDN if the photodetector terminal is the anode and, the second filtering circuit named charge filters function as output signal filters, to obtain individual current signals from each individual photodetector, representing the quantity of light captured by each individual photodetector in the arrangement, giving rise to uncoupled $X_i$ signals.

The bias filters TBF or BBF, as well as the charge filters CF, could be as simple as RC filters, but they should be trimmed to operate at frequency bands separated enough to avoid signal interference between the timing signal and the charge signals.

According to particular embodiments, in the readout network topology, defined above, the time reference signal is the sum of all the cathode terminals of the photodetector in the Single Junction (K).

According to other particular embodiments, in the readout network topology defined above, the time reference signal is the sum of all the cathode terminals of the photodetector at the Single Junction (Pzk), including the delay lines routed on the printed circuit board.

According to particular additional embodiments, in the readout network topology defined above, the timing signal is the sum at the Single Junction (A) of all photodetector anodic terminals.

According to particular additional embodiments, in the readout network topology defined above, the timing signal is the result of the differential signal between the Single Junction (K) of all photodetector cathode terminals and the Single Junction (Pza) of all photodetector anode terminals indirectly wired to Pza.

According to more particular additional embodiments, in the readout network topology defined above, the timing signal is the result of the differential signal between the Single Junction (A) of all photodetector anode terminals and the Single Junction (Pzk) of all photodetector cathode terminals indirectly wired to Pzk.

According to more particular additional embodiments, in the readout network topology defined above, the timing signal is the result of the Single Junction (Pzk) due to the sum of all photodetector cathode terminals indirectly wired to Pzk.

According to particular additional embodiments, in the readout network topology defined above, the timing signal is the result of the Single Junction (Pza) due to the sum of all photodetector anode terminals indirectly wired to Pza.

According to preferred embodiments in readout network topology according to any of the preceding claims, the individual photodetectors are single SiPM devices.

The present invention has a second object a nuclear detector module capable for ToF-PET applications, comprising one or more readout network topologies, having each one a photodetector as defined herein above. (FIG. 13)

The nuclear detector module (FIG. 14) can have a plurality of readout networks arranged, having one column, and a number of p rows, such that the different timing signals obtained from each readout networks are connected to a charge readout schemes in order to obtain energy and position information regarding the plurality of readout networks, (FIG. 9).

The nuclear detector module can further comprise:
a scintillator crystal part facing the photodetector.

a housing to protect the module from external light and mechanical stress,
an analog to digital conversion electronics capable of processing all positioning and energy signals obtained, and transmitting these through a high-speed computer interface to be processed on the fly, or stored in a computer disk, to be later processed, as well as preserving the timing signal.

Since this readout network topology can be piled up, a variety of different detector modules configurations can be manufactured that include a plurality of readout networks according to the present invention, that can be accommodated too in an upper level matrix arrangement, wherein matrix intersections are the readout networks, instead of the individual photodetectors that are the intersections in the readout network individual photodetectors The stacking of several readout networks of this topology also constitutes a readout network of this topology, although it is presented as a higher-level or stacked structure, while from the point of view of the stacked readout network, its constituent readout networks, are lower level readout networks. This can be seen as a fractal structure, as it describes a structure that maintains the same form and functionality at different levels of integration of its stackable components.

According to particular embodiments, (FIG. 9) in a higher-level readout network, q lower-level readout networks are stacked, each of which has a single column and a number of rows (p), to form the higher level readout network. The stacked readout network provides q outputs of time signals that can be acquired separately or through a load network to obtain positioning along the columns, while the number of load signals $X_i$, remains as it was before stacking of the lower level networks, since they overlay (join and sum) all the loading signals of each row along all the columns and can be acquired individually or with any loading scheme, to obtain the position along the p rows, in the same way as in the variants without stacking of readout networks. For example, the overlap in row 2 is as follows: $\Sigma X_{2j}$ (j=1 . . . q).

The arrangement of rows and columns is an arbitrary convention, so rows and columns are interchangeable. According to additional particular embodiments, (FIG. 10) in a higher-level readout network, p lower-level readout networks, each of which has a row and a number of columns (q), are stacked to form the higher level readout network. The stacked readout network provides p time signal outputs that can be acquired separately or through a load network to obtain positioning along the rows, while the number of load signals $X_i$, remains as it was before the stacking of the lower level networks, since they overlay (join and sum) all the loading signals of each column along all the rows and can be acquired individually or with any loading scheme to obtain the position along the rows. columns, in the same way as in the variants without stacking of readout networks. For example, the overlap in column 2 is as follows: $\Sigma X_{i2}$ (i=1 . . . p).

Each of the generic configurations of FIG. 9 and FIG. 10 can be divided into 6 embodiments, if specific configurations of readout networks are used, in the same way that the configurations of FIGS. 2, 4, 5, 6, 7 and 8 are derived from FIG. 1.

The present invention has a third object a ToF-PET System comprising:
a plurality of detector modules as the ones described above, arranged in a mechanical gantry, having a symmetrical configuration, with all modules surrounding and facing the volume of detection that can be covered by the detector modules, surrounding a free volume enough to accommodate a living being or tissue for ToF-PET imaging, and including processing software and synchronization electronics to enable the detection of all signals coming from any module, being charge signals or timing signals.

a coincidence processing electronic module capable to process the timing signals coming from a plurality of modules as described above, to provide the proper matching between multiple combinations of detector modules, allowing to effectively process as a single block, all signals related to any single PET event, no matter which detector module they come from, as well as capable to digitize and transmit all the timing related signals through a high-speed computer interface to be processed on the fly, or stored in a computer disk, to be later processed, including time of flight information of all detected events.

The ToF-PET System can further comprise a software module capable of processing all the data stored in a computer or being received in real time, to provide high quality ToF-PET images, using any computer or digital interface.

The readout network topology for positron emission tomography (PET) with time of flight (TOF) capabilities of the present invention makes it possible to get the belated individual charge information from each photodetector, without affecting the early, fast-transition signals coming from the photodetector parallel common output.

The description and figures essentially describe the topology by means of an undefined number of basic cells and the other components that are not bound to the cell.

All the components bound to the cell will appear below with an index "i", wherein i ranges from 1 to n, being n=p×q, being p the rows and q the columns of the matrix arrangement, and being p and q integers higher than 0.

Often, photodetector signals are first digitized for later processing, but, as better resolution systems require increasing the number of individual detectors in the matrix, this also provokes the increasing of the number of electronic channels, which limits the minimum size achievable photodetector block.

This invention has the advantages of a significant reduction in components, reduction of circuit complexity, reduction of parasitic capacitance and energy consumption.

The readout network topology of the invention uses the typical bias circuit of a photodetector arrangement (a full matrix with p rows and q columns), with some specific modifications, to also extract a unique, accurate and phase-tuned timing signal, regarding the event at any position of the whole photodetector arrangement, no matter what individual photodetector it came from.

The readout network topology here described, is characterized by being properly trimmed and connected to a plurality of light detectors in a matrix configuration, such as SiPM arrangement, extracting timing and charge signals, with a significant reduction in components, circuit complexity, parasitic capacitance and energy consumption, which enables it for ToF-PET applications.

The present invention also has as an object a process to obtain the time and position information from the signals coming from a ToF-PET photodetector, in a detector module of a PET device, the process comprising:

disposing a scintillator crystal in a detector module
disposing a readout network topology as the one defined in the present invention, entering a gamma ray into the module and impinging the scintillator crystal volume, creating a light beam which spreads out everywhere, including the readout network photodetector area, entering the light beam coming from a scintillator crystal into the readout network photodetector area, converting the light beam into a spreaded distribution of electrical signals coming from the whole photodetector area, bringing the first signal detected from any part of the photodetector to a fast amplifier to point it out as the output timing signal, representing the exact instant of the arrival of the gamma ray to the scintillator crystal volume, bringing every one of the electrical signals coming from the whole photodetector area, by means of charge filters to provide uncoupled charge signal outputs compatible with readout electronic circuits commonly used to extract position and energy of the gamma ray.

The process can further comprise handling data from at least two modules, providing information according to claim x obtaining the ToF lines of response required to create a ToF-PET image.

These and other advantages and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Various exemplary embodiments of the subject matter disclosed herein are illustrated in the accompanying drawings in which like reference numerals represent like parts throughout, and in which:

FIG. 13 shows two TOF-PET detector diagrams, with a column low-level readout network topology, which includes SiPM detectors coupled to a scintillating crystal, the one on the left being continuous crystal and the one on the right being pixelated; and FIG. 14 shows two TOF-PET detector diagrams, with a readout network topology stacked in columns, which includes the stacking of detectors like those in FIG. 13, either made of continuous glass as the one on the top, or pixelated as the one on the bottom.

Figure 1:
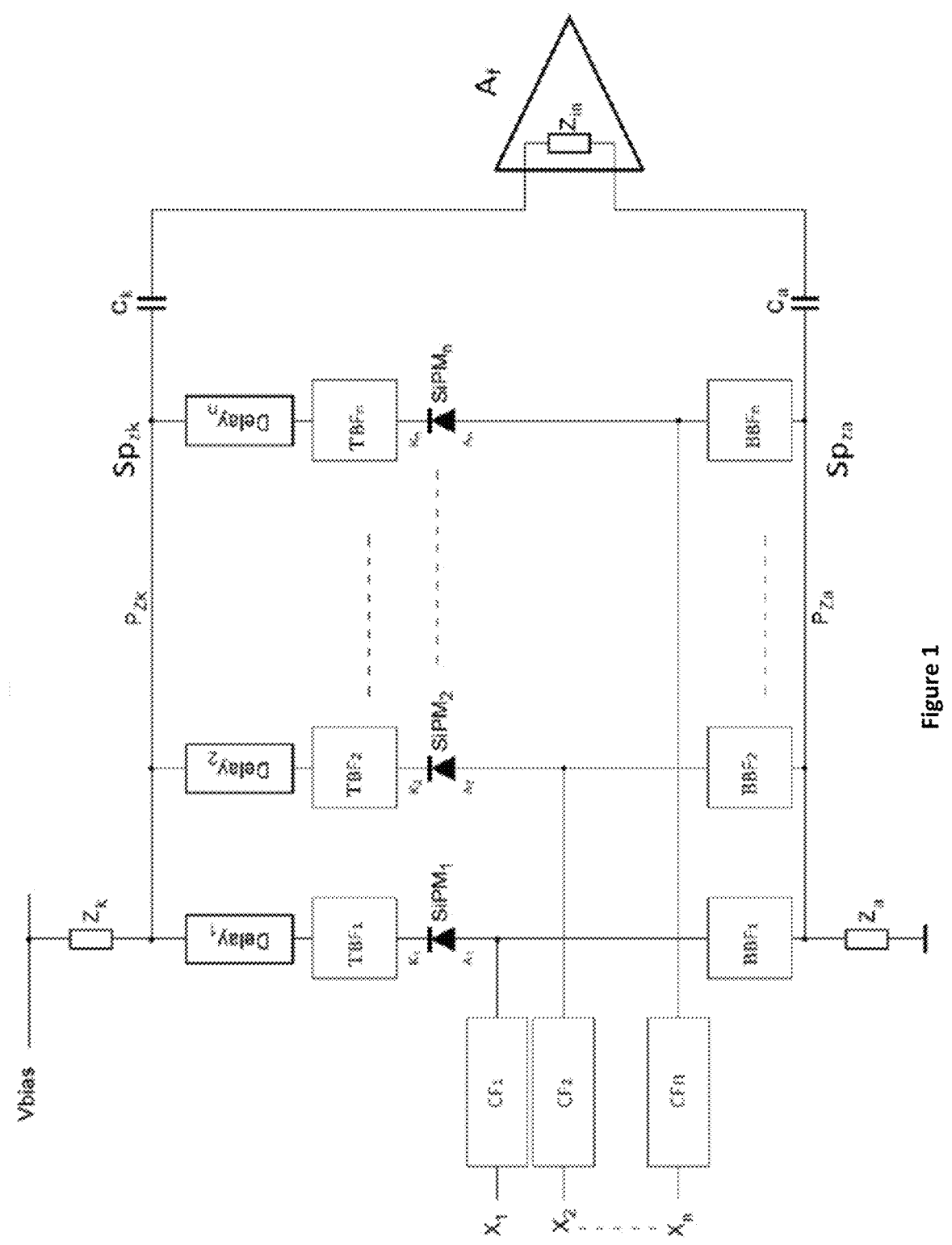
FIG. 1 shows a general diagram of a circuit design topology according to one embodiment of the invention.

In describing the various embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE INVENTION

The various features and advantageous details of the subject matter disclosed herein are explained more fully with reference to the non-limiting embodiments described in detail in the following description.

Turning initially to FIG. 1, The basic cell of the present invention includes a repeatable pack of components and connections such as that labelled at FIG. 1, as the SiPM the SiPM cathode K, the SiPM anode A, the Delay, the bias filters TBF and BBF, the output filter CF, the output signal X, and other components from specific embodiments related to other figures (Rf, Cf, Ce, Re, etc).

The cells in the present invention are arranged in a matrix of n elements, wherein n=pxq, being p: rows and q columns. We may call i, to an index to make reference to all cells, provided that ii ranges from 1 to n.

So, according to this convention, it is possible to make reference to any component of a Cell in the photodetector arrangement, using its own generic name followed by this index, such as $SiPM_i$, $K_i$, $A_i$, $TBF_i$, $BBF_i$, $CF_i$, etc.

In the readout network topology (FIG. 1 Circuit design topology), all similar terminals of one of the two types of the photodetector terminals (either the anodic ones or the cathodic ones) are wired to a Single Junction at the PCB (for example at Pzk or Pza), wherein the Single Junction is further split into two routes for further connections.

On the one hand, a first route connects the Single Junction, by means of a specific bias impedance ($Z_k$), to the proper source polarity (Vbias). The bias impedance is working as part of the photodetector bias circuit, and its resistance is set to be less than 10% compared to the resistance of the rest of the route from the Single Junction to GND, so that the voltage at the Single Junction is virtually the same as the voltage of the source which is feeding the other terminal of the impedance, preventing the individual photodetector capacitances to be added.

We are using here, by simplicity, the specific labeling of the FIG. 1 Circuit design topology, which is set according to the specific voltage polarity setting (however, the polarity can be reversed). So, this polarity is Vbias, because the terminals wired to the Single Junction are the cathodes, otherwise it should be GND if the wired terminals were the anodes.

In the same way, filters are established in the polarization route from the photodetector both towards Vbias and towards GND and their parameters are established so that the filters can be canceled or activated according to the particular embodiment. In particular, in this invention we deal with configurations where the filters are set alternately, either on the polarization route between photodetector and Vbias (in which case we call it TBF) or they are set on the polarization route between photodetector and GND (in which case we call it BBF). In the different particular embodiments, only the filters that are actually active will be represented.

For the general case of this topology, the power connections: Vbias and GND are considered exchangeable provided that the components polarities are adjusted accordingly, so that different configurations are obtained on the same basis, representing different signal and power source polarities (positive, negative and differential), as we will see below in a set of different embodiments. Furthermore, giving specific limit values for some components, will turn the general circuit into a specific embodiment of the invention.

On the other hand, a second route feeds the unified signal created at the Single Junction, into a fast amplifier, obtaining a single timing signal regarding the complete photodetector arrangement, no matter which individual photodetector it comes from.

The bias impedance is labelled $Z_a$ when it is placed in the unified route from the photodetector anodes to Ground (GND), and it is labelled $Z_k$ when it is placed in the unified route from the photodetector cathodes to Vbias.

The Single Junction may appears near different source polarities, and connecting different photodetector terminals (for example, SiPM terminals), according to the specific embodiment used, based on the described circuit topology. When the Single Junction is wiring anodic terminals coming directly from the photodetector arrangement it is simply labelled A, while it is labelled K, when the Single Junction is connecting the cathode terminals coming directly from the photodetector matrix (e.g. SiPM).

Moreover, in some embodiments there is some circuitry replicated between each photodetector terminal that we want to join, and the effective PCB point at the Single Junction, where we wire up all together, so that we have an indirect connection between the Single Junction and the photodetector arrangement terminals.

When the Single Junction is wiring connections that are coming indirectly from the photodetector arrangement anodic terminals it is labelled as $P_{za}$, while it is labelled as $P_{zk}$, when the Single Junction is wiring the cathode terminals coming indirectly from the photodetector (as for example SiPM) arrangement.

After these clarifications, it follows that, when we refer in general to the unified timing signal that is carried from the Single Junction point (or points) into the fast amplifier to obtain a single timing signal regarding the whole photodetector, no matter which individual photodetector it comes from, this also refers to all other equivalent points that work as the Single Junctions in the different embodiments, labelled as A, K, $P_{za}$ and $P_{zk}$. According to the embodiments that we will describe below in detail, we may obtain single polarity timing signals from any of these labelled points or differential timing signals using valid combinations of these labelled points, as we will see below.

The routes to each individual photodetector are tuned for synchronization of the starting edges of any signal coming from any individual photodetector. These routes could be represented with delay lines (Delay$_i$), (i ranges from 1 to n, and n=pxq in a matrix) in series with each individual photodetector.

All the other similar photodetector terminals, that were not directly or indirectly wired to the Single Junction, are separately connected to two connection types: On the one hand, these are connected to the other power source polarity by means of a parallel set of individual filtering circuits (BBF$_i$), (bias filters) (and eventually including another bias impedance (either $Z_a$ or $Z_k$) in series with the BBF; filters, and on the other hand, these are extracted as independent output signals (X$_i$) by means of a parallel set of individual filtering circuits (CF$_i$) (charge filters), that can be used to feed any readout network scheme to obtain X and Y coordinates, Depth-of-Interaction values and energy.

The combined adjustment of the charge filters CF$_i$ and the bias filters BBF$_i$ and TBF; the bias impedances, $Z_k$ and $Z_a$, the capacitances of the individual photodetectors and the routed delays (Delay$_i$), through each connection of the individual photodetectors, to obtain an optimal circuit response, allowing us to separately obtain information about the captured charge and the position of the individual photodetectors involved in the event, as well as a single, accurate, phase tuned timing signal, regarding the same event at any part of the whole photodetector, no matter which individual photodetector it came from.

Furthermore, a fast amplifier is electrically coupled to the parallel common output of the photodetector, where the single timing signal is generated. This amplifier is electrically coupled to this timing signal, is characterized by a fast response and a low input impedance, creating a low-impedance path for fast transition signals, which is going to improve (to reduce) the total parasitic capacitance of the parallel individual photodetectors arrangement, improving the time response of the whole photodetector. Also, the readout electronics of the invention creates a reduced number of positioning signals, from (pxq) signals to (p+q) signals.

The Single Junction is connected by means of a specific bias impedance, to the proper source polarity (Vbias). The bias impedance is working as part of the photodetector bias circuit, and its resistance is set to be less than 10% compared to the resistance of the rest of the route from the Single Junction to GND, so that the voltage at the Single Junction is virtually the same as the voltage of the source which is feeding the other terminal of the impedance, preventing the individual photodetector capacitances to be added. One has to be aware that the resistance is the real part of the complex numeric value of the impedance. In these conditions, the terminals of the whole photodetector are virtually connected between Vbias and GND, minimizing their mutual interferences, with a behavior similar to that if they were not in a parallel connection, so, their capacitances are nor added from the point of view of the X$_i$ signals.

On the other hand, from the point of view of the timing signal, the bias impedance together with the amplifier A$_f$, creates a high frequency band-pass filter that absorbs and amplifies any starting edge of a fast signal coming from any individual photodetector to provide a single common timing signal.

In the case of the parallel set of charge filters, these are trimmed to obtain at each one of the different X$_i$ outputs, a bandwidth apart enough from that of the timing signal, but also at a lower frequency, in order to be able to obtain an accurate measurement of the charges involved in the measured event, without regarding the time consumed to accomplish this. These outputs represent individual uncoupled signals from each individual photodetector, that can be fed to other suitable readout networks, or different electronic circuits, that collect all the charges of the photodetector, according to the sensing scheme used to obtain values representing magnitudes such as planar X & Y spatial coordinates, the event energy and the Depth-of-Interaction.

In the case of the bias filters BBF$_i$, TBF$_i$ those are trimmed, together with the bias impedance, to match individually the bias current of each individual photodetector and to obtain at the Single Junction, a very high and narrow frequency response, close to the highest frequency components of the signal coming from the photodetector, in order to generate an accurate and early time response output, without affecting the belated signals (X$_i$), which contain charge information and will appear later. The belated signal is a high frequency signal too, but having lower bandwidth than the time-response signal, allowing us to separate both by frequency filtering.

As a result, a very fast output signal will appear at the Single Junction, during a very short time frame as a response to any high-speed transition signal coming from any of the individual photodetectors (such as SiPM).

The resulting single timing signal is injected to the mentioned fast amplifier, which is designed to operate in the highest frequency band of the photodetector response, to generate a single, time-accurate and early time response, without affecting the belated signal with charge information, directed by separate paths, following each of the other SiPM terminals.

Examples 1 and 2

Figure 2:
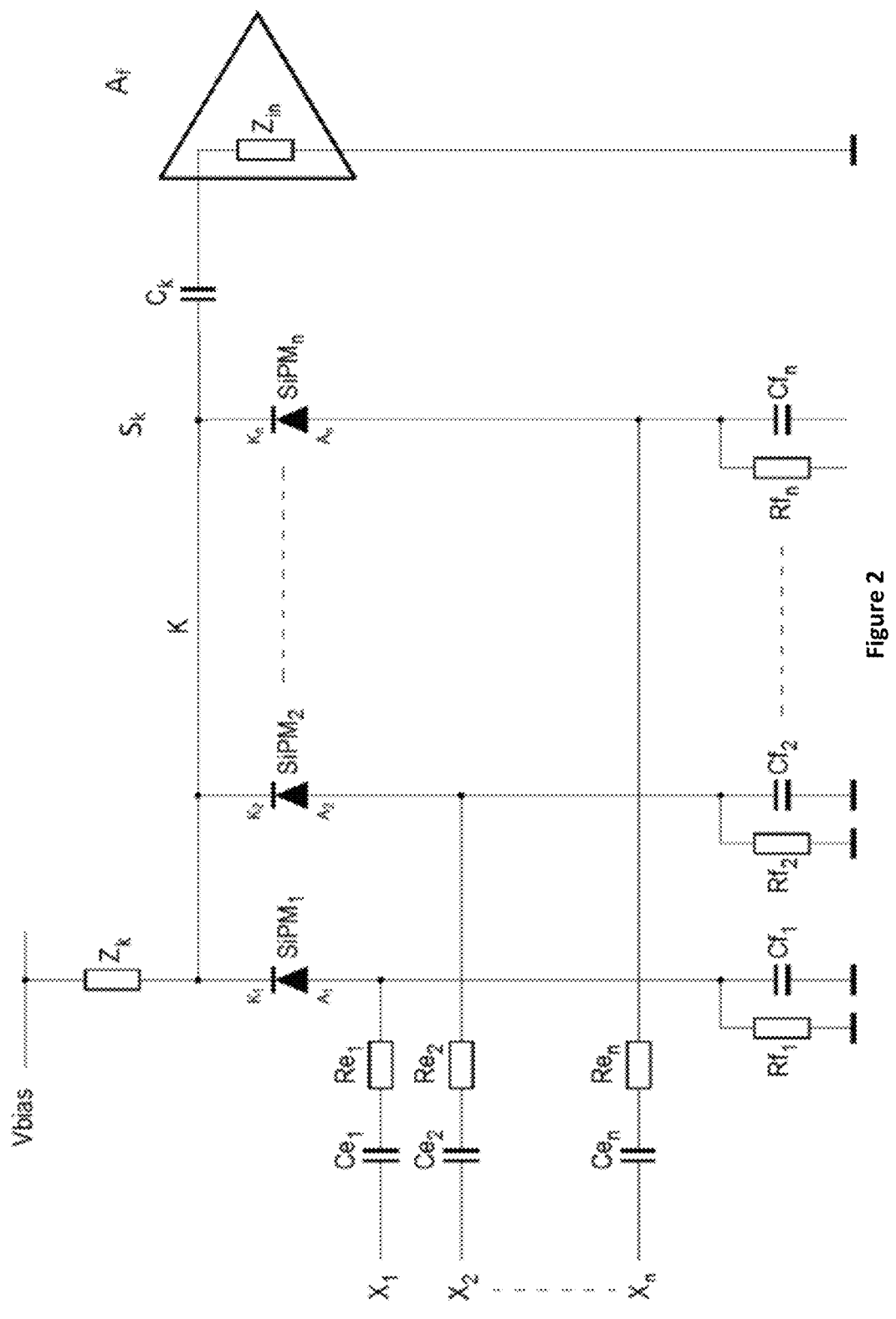
FIG. 2 illustrates a circuit design embodiment where the timing signal is obtained at the Single Junction (K) of all SiPM cathode terminals.

In a specific embodiment of the design (FIG. 2), all the SiPM$_i$ detectors (SiPM$_1$ to SiPM$_n$) are connected in such a way that, all the cathodic terminals (K$_i$) are wired together to obtain the Single Junction K, which is then connected to the bias source by means of a single impedance ($Z_k$), while all the anodic terminals (A$_i$) are separately connected to two connection types: On the one hand, these are separately connected to GND by means of a parallel set of individual filtering circuits (Cf$_i$||Rf$_i$) working as the BBF$_i$ filters at FIG. 1. On the other hand, these are extracted as independent output signals (X$_i$) by means of a parallel set of individual filtering circuits ($C_{ei}$-$Re_i$) working as the $Cf_i$ filters of FIG. 1. In this case, the impedance $Z_a$ of the FIG. 1 is 0, thus shortened to GND, and the $TBF_i$ filters are cancelled by shortening the filter resistance.

The mentioned filtering circuits are tuned in such a way that for high-speed transition signals, all the individual photodetectors virtually share the same connection points (parallel connection between K and GND) allowing the generation of a very fast signal $S_K$ at the unified terminal K, representing the time response of the whole photodetector, no matter which individual photodetector the signal comes from. The signal $S_K$ is used to feed a fast amplifier ($A_f$), designed to operate specifically at the highest frequency band of the individual photodetectors response, in order to generate an accurate and early time response output, without affecting the belated signals ($X_i$), which contain charge information and will appear later following each of the other photodetector terminals $A_i$, in the other route, through the parallel set of individual filtering circuits ($Ce_i$-$Re_i$).

Figure 3:
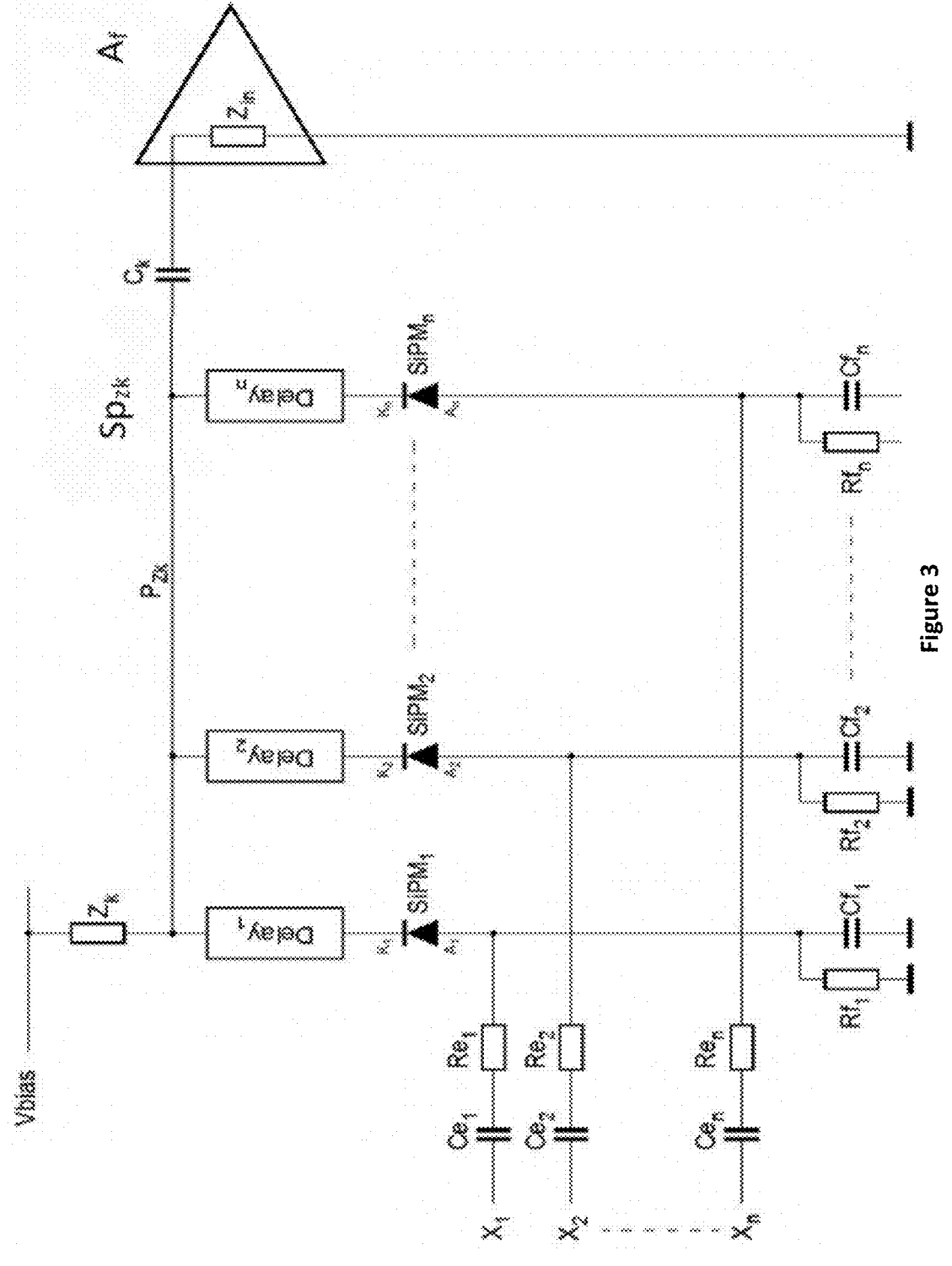
FIG. 3 illustrates a circuit design embodiment where the timing signal is obtained at the Single Junction ($P_{zk}$) of all SiPM cathodic terminals, but including the PCB routed delay lines in the schematic.

All individual photodetectors printed circuit board (PCB) routing connections are "time delay tuned" in a way that the starting edges of any signal coming from any individual photodetector will arrive synchronized to the circuit point where the single common timing signal is obtained, (K, for this case). This could be represented as a delay line inserted in series connection to each individual photodetector, so that the circuit of FIG. 2 becomes FIG. 3. All the schematics hereafter are considered to include the PCB routed delay lines in series with each individual photodetector, although they will not be drawn in the schematics for simplicity.

Example 3

Figure 4:
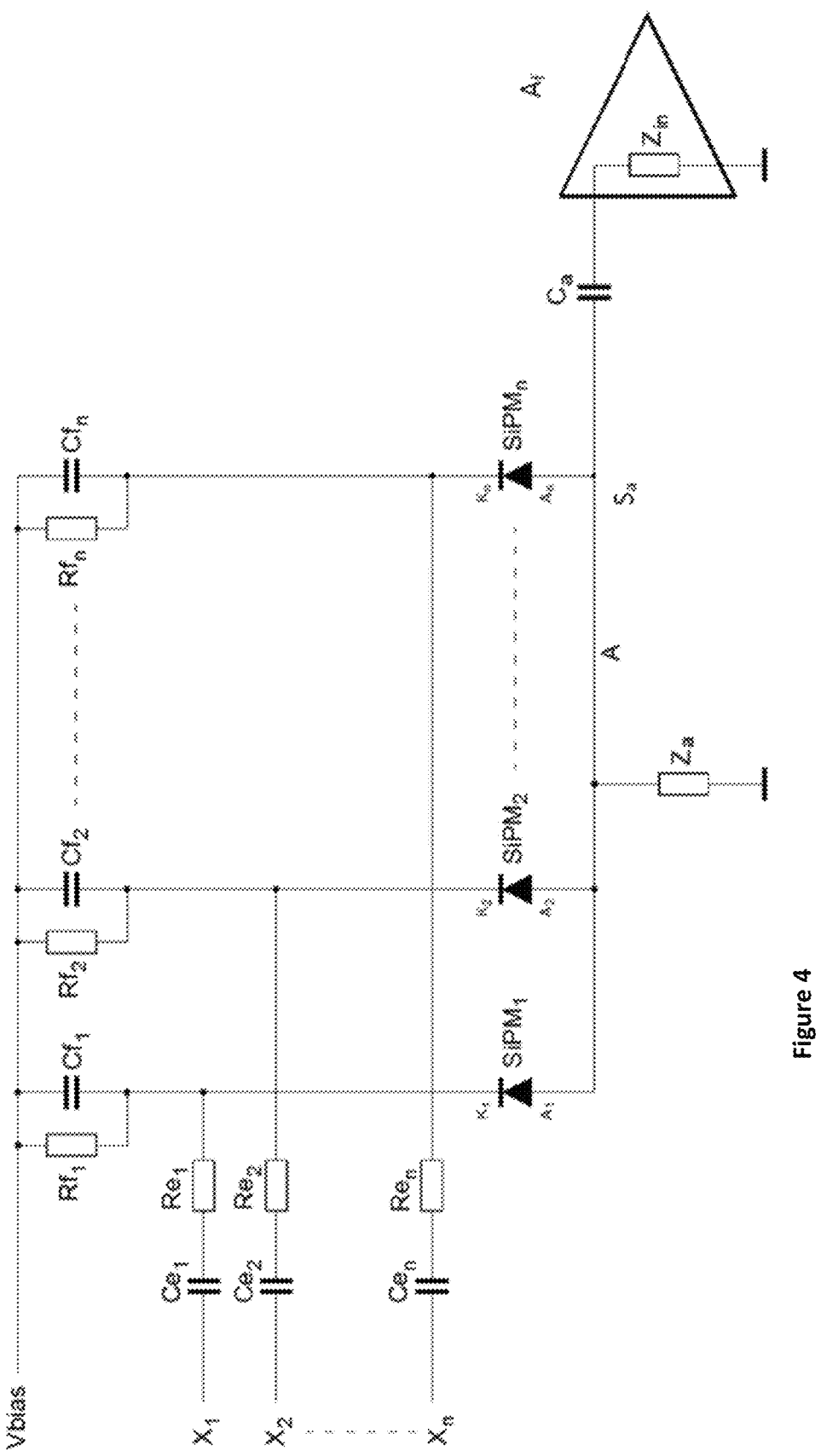
FIG. 4 illustrates a circuit design embodiment where the timing signal is obtained at the Single Junction (A) of all SiPM anodic terminals.

In a second specific embodiment of the design (FIG. 4]), all the SiPM$_i$ photodetectors (SiPM$_1$ to SiPM$_n$) are connected in such a way that, all the anodic terminals ($A_i$) (i ranges from 1 to n) are wired together to obtain the Single Junction A, which is then connected to GND by means of a single impedance ($Z_a$), while all the cathodic terminals ($K_i$) are separately connected to two connection types: On the one hand, these are separately connected to the bias power source by means of a parallel set of individual filtering circuits ($Cf_i$‖$Rf_i$), working as the TBFi filters at the FIG. 1. On the other hand, these are extracted as independent output signals ($X_i$) by means of a parallel set of individual filtering circuits ($Ce_i$-$Re_i$).

In this case, the impedance Zk of the FIG. 1 is 0, thus shortened to Vbias, and the BBF$_i$ filters are cancelled by shortening the filter resistance.

The mentioned filtering circuits are tuned in such a way that for high-speed transition signals, all the individual photodetectors virtually share the same connection points (parallel connection between A and Vbias), allowing the generation of a very fast signal $S_a$ at the unified terminal A representing the time response of the whole photodetector, no matter which individual photodetector the signal comes from. The signal $S_a$ is used to feed a fast amplifier $A_f$, designed to operate specifically at the highest frequency band of the photodetector response, in order to generate an accurate and early time response output, without affecting the belated signals (Xi) which contain charge information, and will appear later, following each of the other individual photodetector terminals $K_i$, in the other route, through the parallel set of individual filtering circuits ($Ce_i$-$Re_i$).

Example 4

Figure 5:
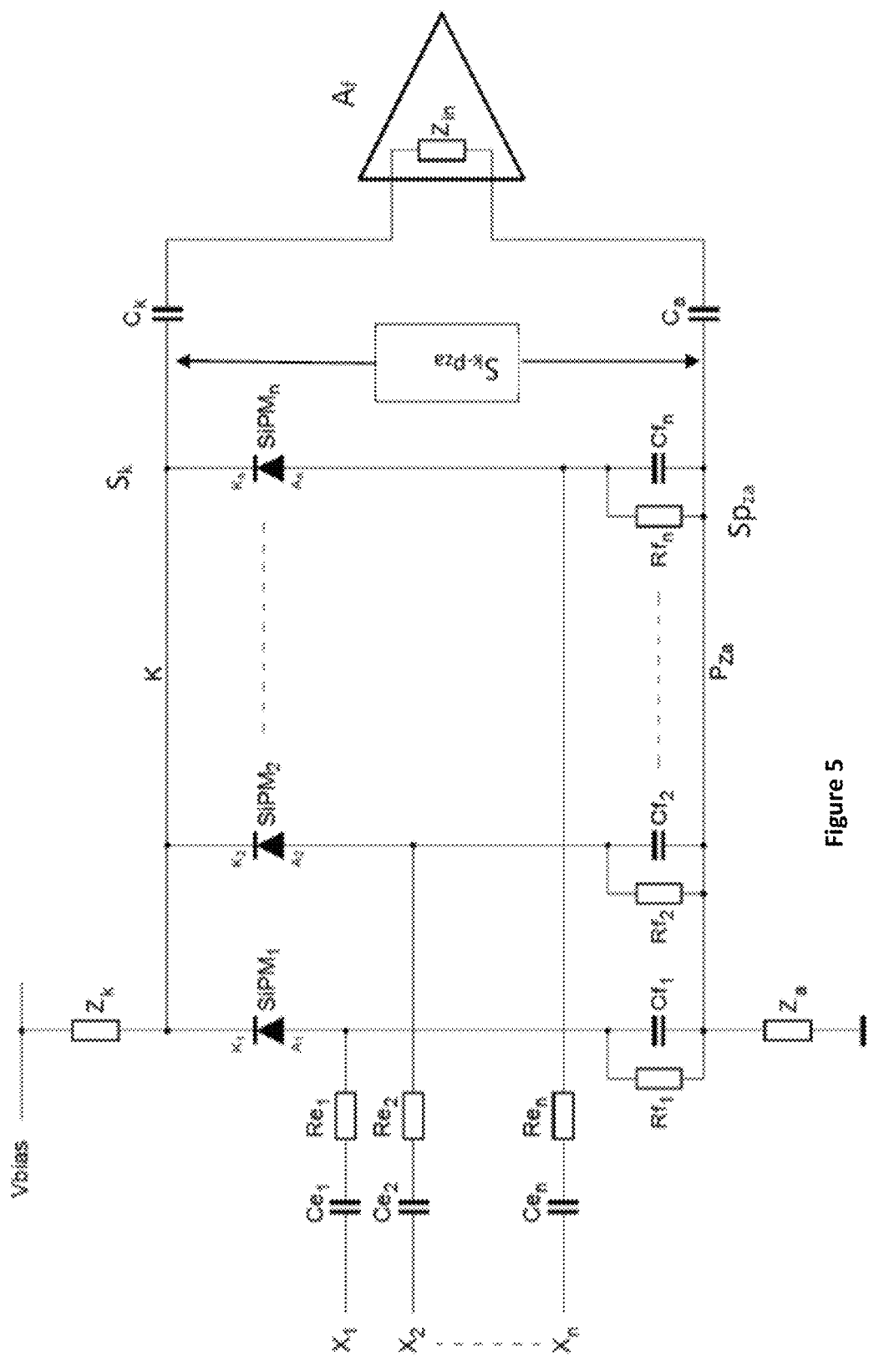
FIG. 5 illustrates a circuit design embodiment where the timing signal is obtained as the differential signal between the Single Junction (K) of all SiPM cathodic terminals and the Single Junction ($P_{za}$) of all SiPM anodic terminals indirectly wired.

In a third specific embodiment of the design (FIG. 5]), all the individual photodetectors (SiPM$_1$ to SiPM$_n$) are connected in such a way that, all the cathodic terminals ($K_i$) (i ranges from 1 to n) are wired together to obtain the Single Junction K, which is further connected to the bias source by means of a single impedance ($Z_k$), while all the anodic terminals ($A_i$) are separately connected to two connection types: On the one hand, these are separately connected to a Single Junction ($Pz_a$) by means of a parallel set of individual filtering circuits ($Cf_i$‖$Rf_i$) working as the BBF$_i$ filters of the FIG. 1, and then connected from here to GND by means of a single impedance $Z_a$. On the other hand, these are extracted as independent output signals ($X_i$) by means of a parallel set of individual filtering circuits ($Ce_i$-$Re_i$). In this case the TBF$_i$ filters are cancelled by shortening the filter resistance.

The mentioned filtering circuits are tuned in such a way that for high-speed transition signals, all the individual photodetectors virtually share the same connection points (parallel connection between K and $Pz_a$), allowing the generation of a differential very fast signal $S_{K\text{-}PZA}$ between the unified terminal K, and the unified terminal $P_{Z4}$ representing the time response of the whole photodetector, no matter which photodetector the signal comes from. The signal $S_{K\text{-}Pza}$ is used to feed differentially a fast amplifier ($A_f$), designed to operate specifically at the highest frequency band of the individual photodetectors response bandwidth, in order to generate an accurate and early time response output, without affecting the belated signals (Xi) which contain charge information, and will appear later, following each of the other photodetector terminals $A_i$.

Example 5

Figure 6:
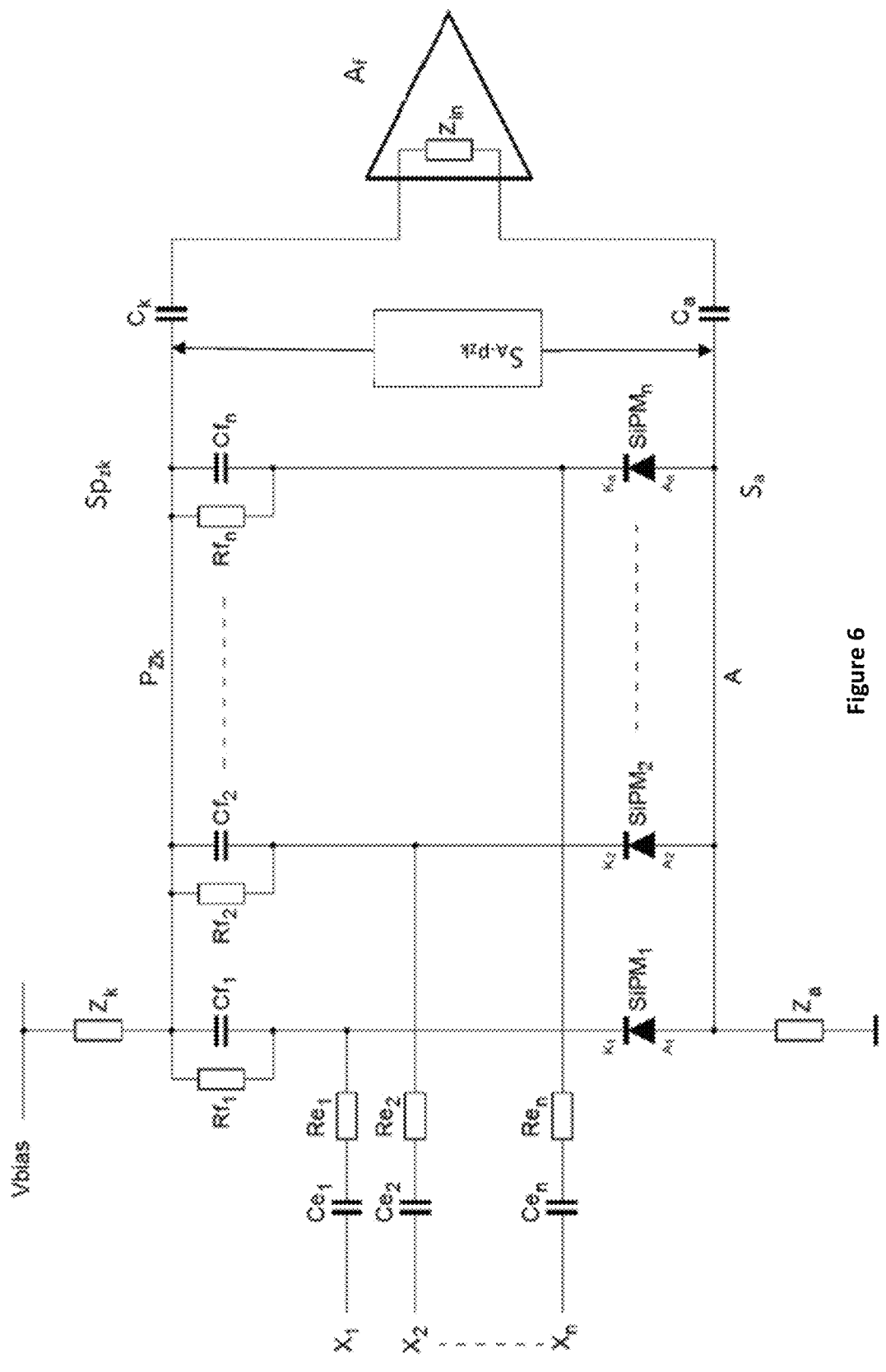
FIG. 6 illustrates a circuit design embodiment where the timing signal is obtained as the differential signal between the Single Junction (A) of all SiPM anodic terminals and the Single Junction ($P_{zk}$) of all SiPM cathodic terminals indirectly wired.

In a fourth specific embodiment of the design (FIG. 6), all the individual photodetectors (SiPM$_1$ to SiPM$_n$) are connected in such a way that, all the anodic terminals ($A_i$) (i ranges from 1 to n) are wired together to obtain the Single Junction A, which is further connected to GND by means of a single impedance ($Z_a$), while all the cathodic terminals ($K_i$) are separately connected to two connection types: On the one hand, these are separately connected to a Single Junction ($Pz_k$) by means of a parallel set of individual filtering circuits ($Cf_i$‖$Rf_i$) working as the TBF$_i$ filters at the FIG. 1, and then connected from here to Vbias by means of a single impedance $Z_k$. On the other hand, these are extracted as independent output signals ($X_i$) by means of a parallel set of individual filtering circuits ($Ce_i$-$Re_i$). In this case the BBF$_i$ filters are cancelled by shortening the filter resistance.

The mentioned filtering circuits are tuned in such a way that for high-speed transition signals, all the individual photodetectors virtually share the same connection points (parallel connection between A and $P_{Zk}$), allowing the generation of a differential very fast signal $S_{A\text{-}Pzk}$ between the unified terminal A, and the unified terminal $P_{Zk}$ representing the time response of the whole photodetector, no matter which individual photodetector the signal comes from. The signal $S_{A\text{-}Pzk}$ is used to feed differentially a fast amplifier ($A_f$), designed to operate specifically at the highest frequency band of the detector response, in order to generate an accurate and early time response output, without affecting the belated signals ($X_i$) which contain charge information, and will appear later, following each of the other photodetector terminals $K_i$.

Example 6

Figure 7:
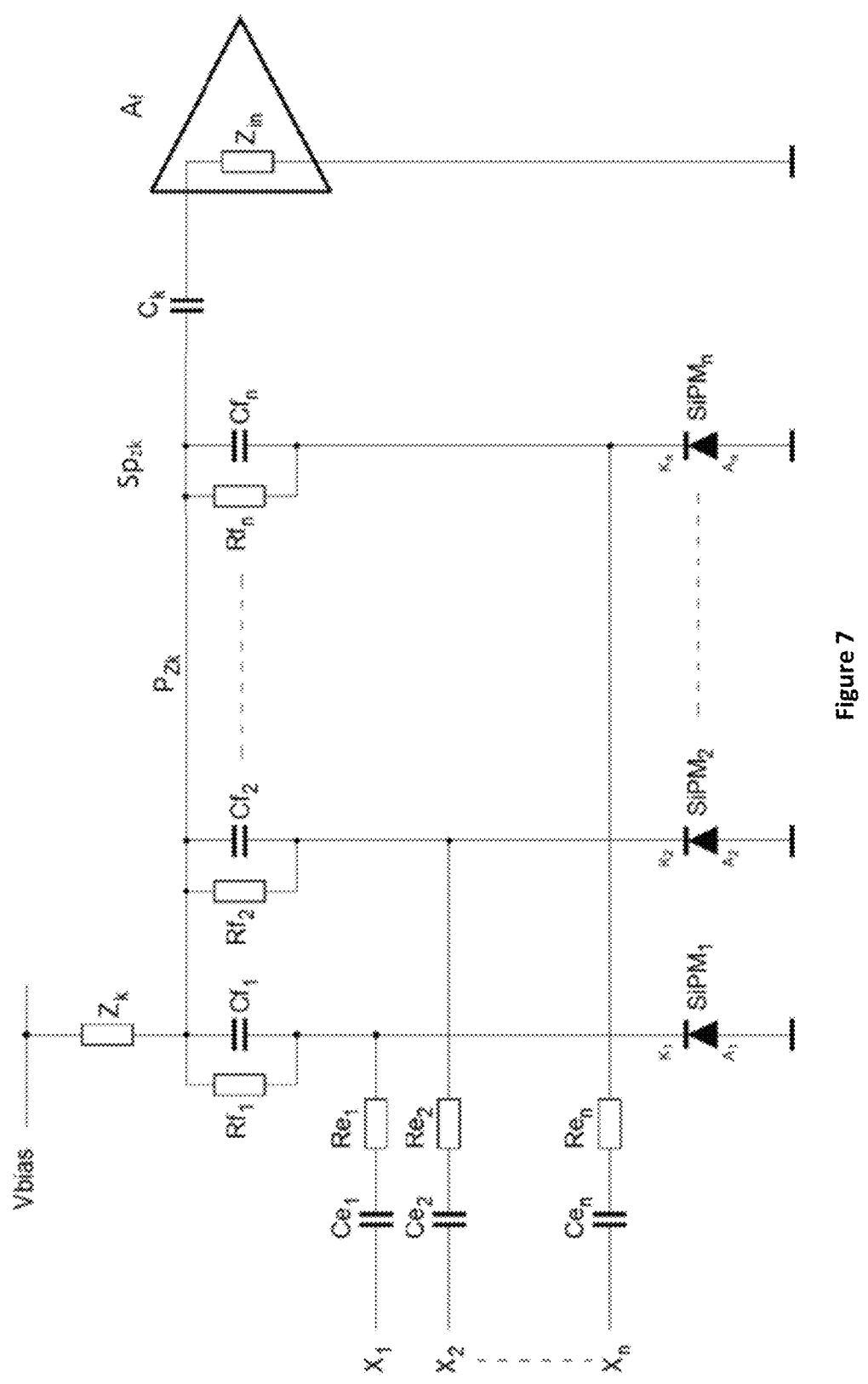
FIG. 7 illustrates a circuit design embodiment where the timing signal is obtained at the Single Junction ($P_{zk}$) of all SiPM cathodic terminals indirectly wired.

In a fifth specific embodiment of the design (FIG. 7), all the individual photodetectors (SiPM$_1$ to SiPM$_n$) are connected in such a way that, all the anodic terminals (A$_i$) (i ranges from 1 to n) are wired to GND, while all the cathodic terminals (K$_i$) are separately connected to two connection types: On the one hand, these are separately connected to a Single Junction (Pz$_k$) by means of a parallel set of individual filtering circuits (Cf$_i$||Rf$_i$) working as the TBF$_i$ filters of the FIG. 1, and further connected from here to Vbias by means of a single impedance Z$_k$. On the other hand, these are extracted as independent output signals (X$_i$) by means of a parallel set of individual filtering circuits (Ce$_i$-Re$_i$). In this case, the impedance Za of the FIG. 1 is 0, thus shortened to Vbias, and the BBF$_i$ filters are cancelled by shortening the filter resistance.

The mentioned filtering circuits are tuned in such a way that for high-speed transition signals, all the individual photodetectors virtually share the same connection points (parallel connection between P$_{Zk}$ and GND), allowing the generation of a very fast signal S$_{Pzk}$ at the unified terminal P$_{Zk}$ representing the time response of the whole photodetector, no matter which photodetector the signal comes from. The signal S$_{Pzk}$ is used to feed a fast amplifier (A$_f$), designed to operate specifically at the highest frequency band of the detector response, in order to generate an accurate and early time response output, without affecting the belated signals (Xi) which contain charge information, and will appear later, following each of the photodetector terminals K$_i$, in the other route, through the parallel set of individual filtering circuits (Ce$_i$-Re$_i$).

Example 7

Figure 8:
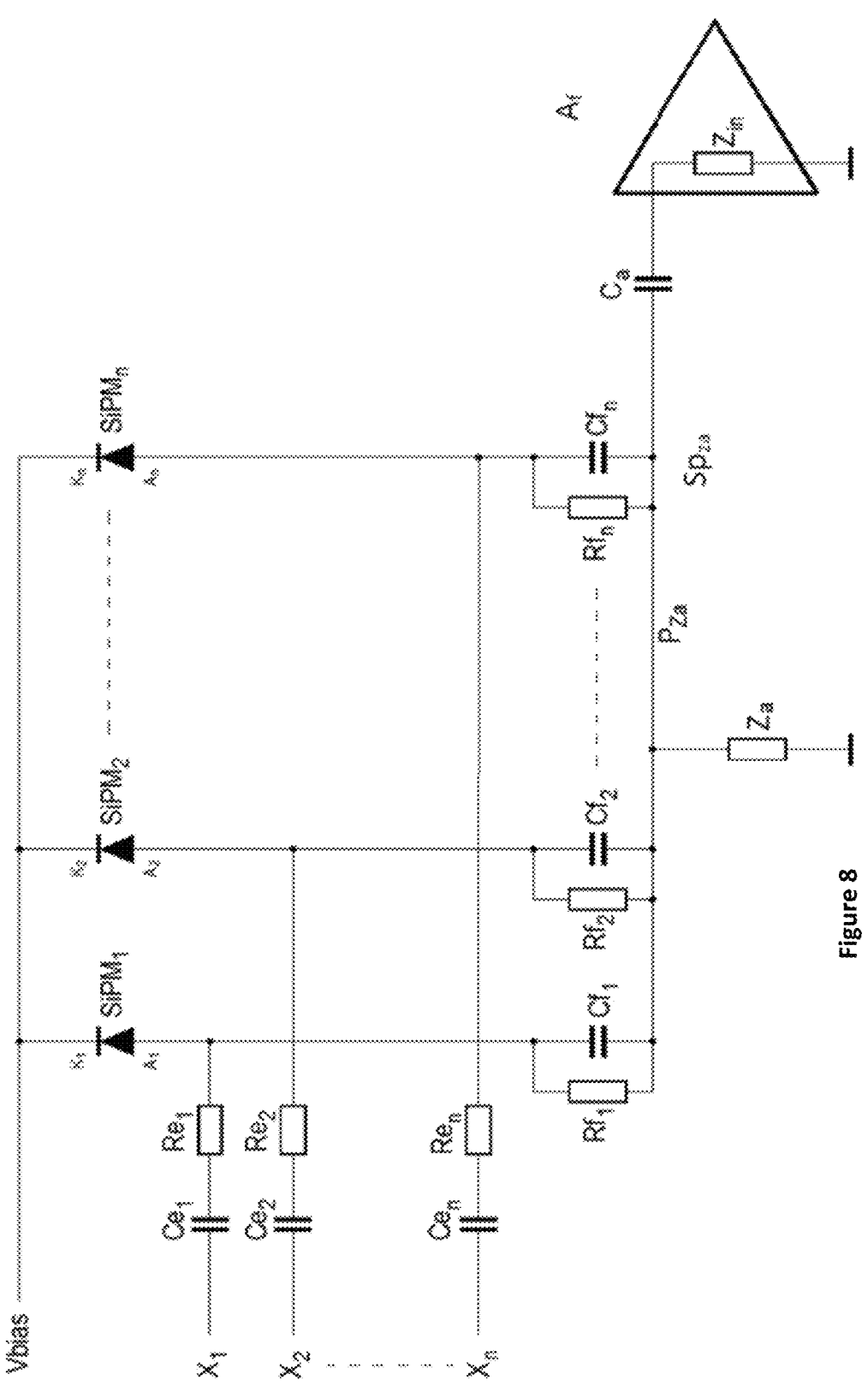
FIG. 8 illustrates a circuit design embodiment where the timing signal is obtained at the Single Junction ($P_{za}$) of all SiPM anode terminals indirectly wired.

In a sixth specific embodiment of the design (FIG. 8), all the individual photodetectors (SiPM$_1$ to SiPM$_n$) are connected in such a way that, all the cathodic terminals (K$_i$) (i ranges from 1 to n) are wired to Vbias, while all the anodic terminals (A$_i$) are separately connected to two connection types: On the one hand, these are separately connected to a Single Junction (Pz$_a$) by means of a parallel set of individual filtering circuits (Cf$_i$||Rf$_i$) working as the BBF; filters of the FIG. 1, and further connected from here to GND by means of a single impedance Z$_a$. On the other hand, these are extracted as independent output signals (X$_i$) by means of a parallel set of individual filtering circuits (Ce$_i$-Re$_i$). In this case, the impedance Zk of the FIG. 1 is 0, thus shortened to Vbias, and the TBFi filters are cancelled by shortening the filter resistance.

The mentioned filtering circuits are tuned in such a way that for high-speed transition signals, all the individual photodetectors virtually share the same connection points (parallel connection between Vbias and P$_{Za}$), allowing the generation of a very fast signal S$_{Pza}$ at the unified terminal P$_{Za}$ representing the time response of the whole photodetector, no matter which individual photodetector the signal comes from. The signal S$_{Pza}$ is used to feed a fast amplifier (A$_f$), designed to operate specifically at the highest frequency band of the detector response, in order to generate an accurate and early time response output, without affecting the belated signals (X$_i$) which contain charge information, and will appear later, following each of the photodetector terminals A$_i$, in the other route, through the parallel set of individual filtering circuits (Ce$_i$-Re$_i$).

Example 8

Figure 9:
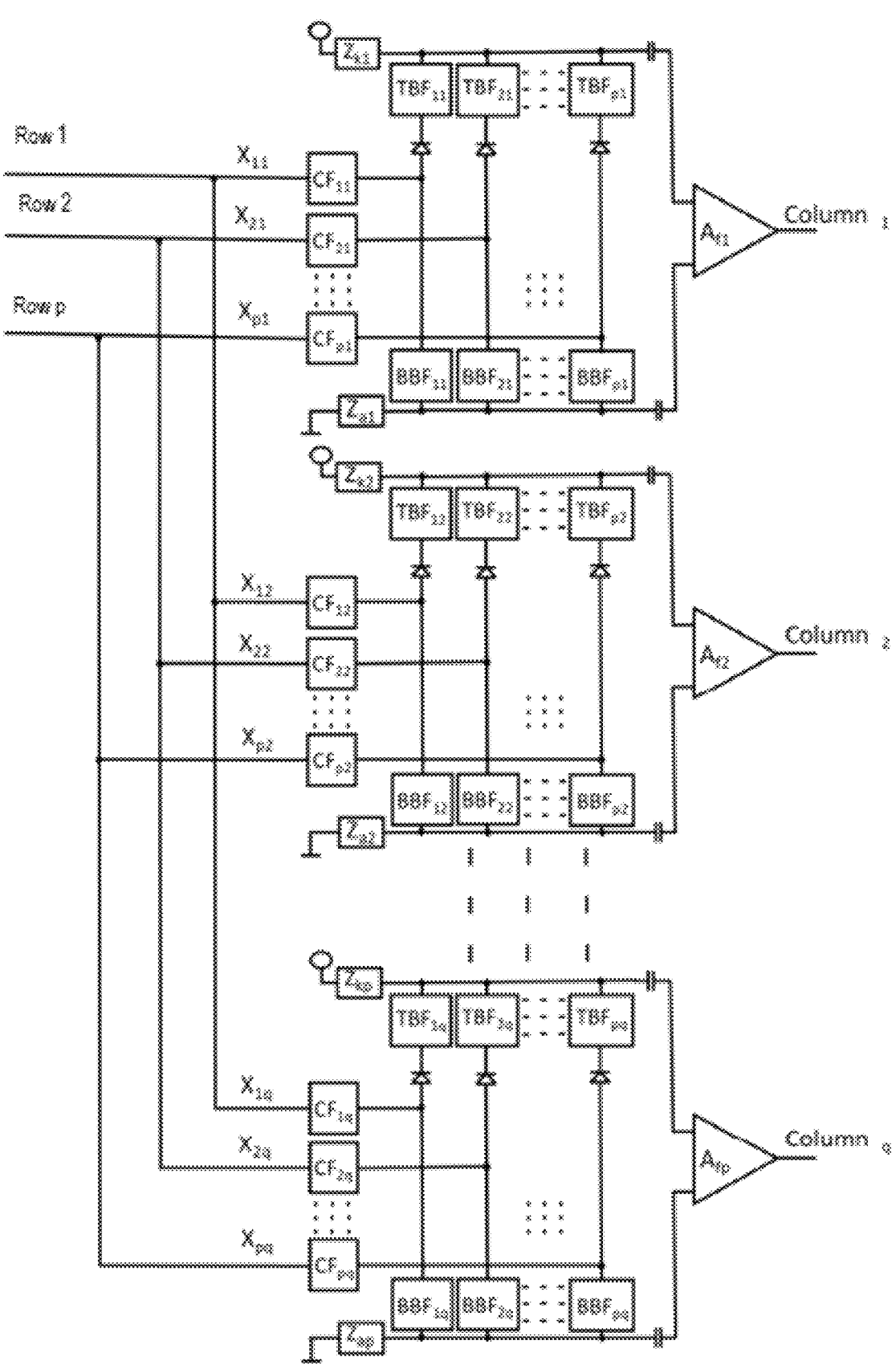
FIG. 9 shows a general diagram of the readout network topology according to one embodiment of the invention, similar to that of FIG. 1, wherein the readout network is made up of the stacking of several lower-level readout networks arranged in the form of columns.
Figure 10:
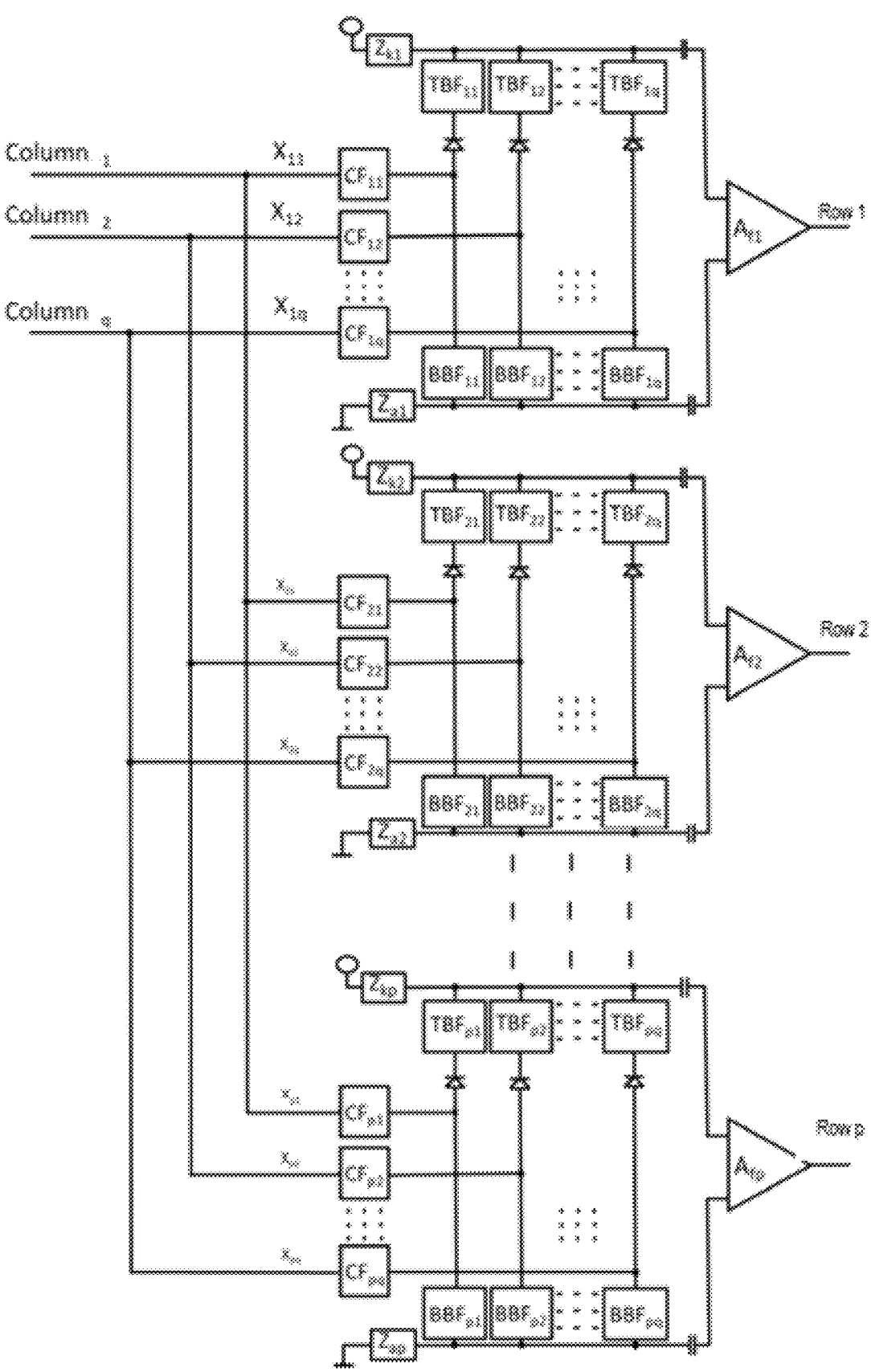
FIG. 10 shows the diagram of the same topology seen in FIG. 9, but by means of the stacking of lower level readout networks arranged in the form of rows.

In a seventh design embodiment (FIG. 9), we use the stacking capacity of this read network topology, described in the second object of the invention, to show a package of 6 design variants, equivalent to the 6 embodiments described in the 7 previous examples. The difference consists in using several lower-level readout networks, stacked to form a higher-level readout network, either by stacking columns (FIG. 9) or by stacking rows (FIG. 10). In all cases, both the constituent lower-level networks and the obtained higher-level networks are part of the readout network topology disclosed here.

Any of the variants of readout networks, such as the 6 already described in the previous examples, can serve as a lower level readout network (or building block) from which the stacked readout networks of example 8 are obtained. There is also a set of filter variants that can be placed in place of the blocks called TBF, BBF, and CF, beyond the 6 particular schemes shown in FIGS. 3 to 8. From this arises a wide combinatorics of particular embodiments, all of which maintain the topology described. Representative variants of the readout network topology are shown.

Figure 11:
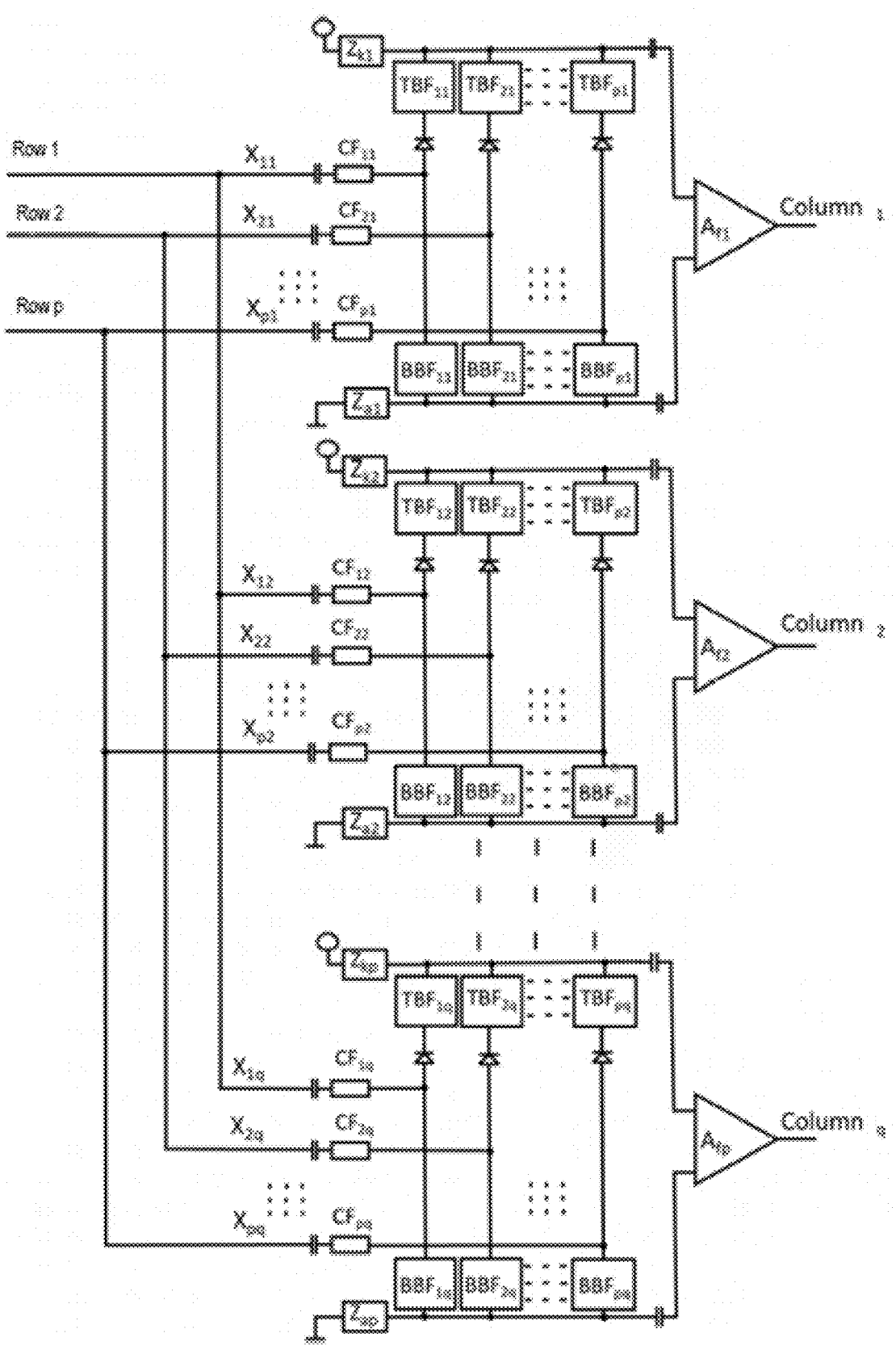
FIG. 11 shows a particularization of the more general scheme of FIG. 9, in which the CF filters are schematized as C-R networks in series, in the same way as in FIGS. 2 to 8, with the exception that we maintain the names of each filter in the form $CF_{ij}$, as they are in FIG. 9 from which they are derived.
Figure 12:
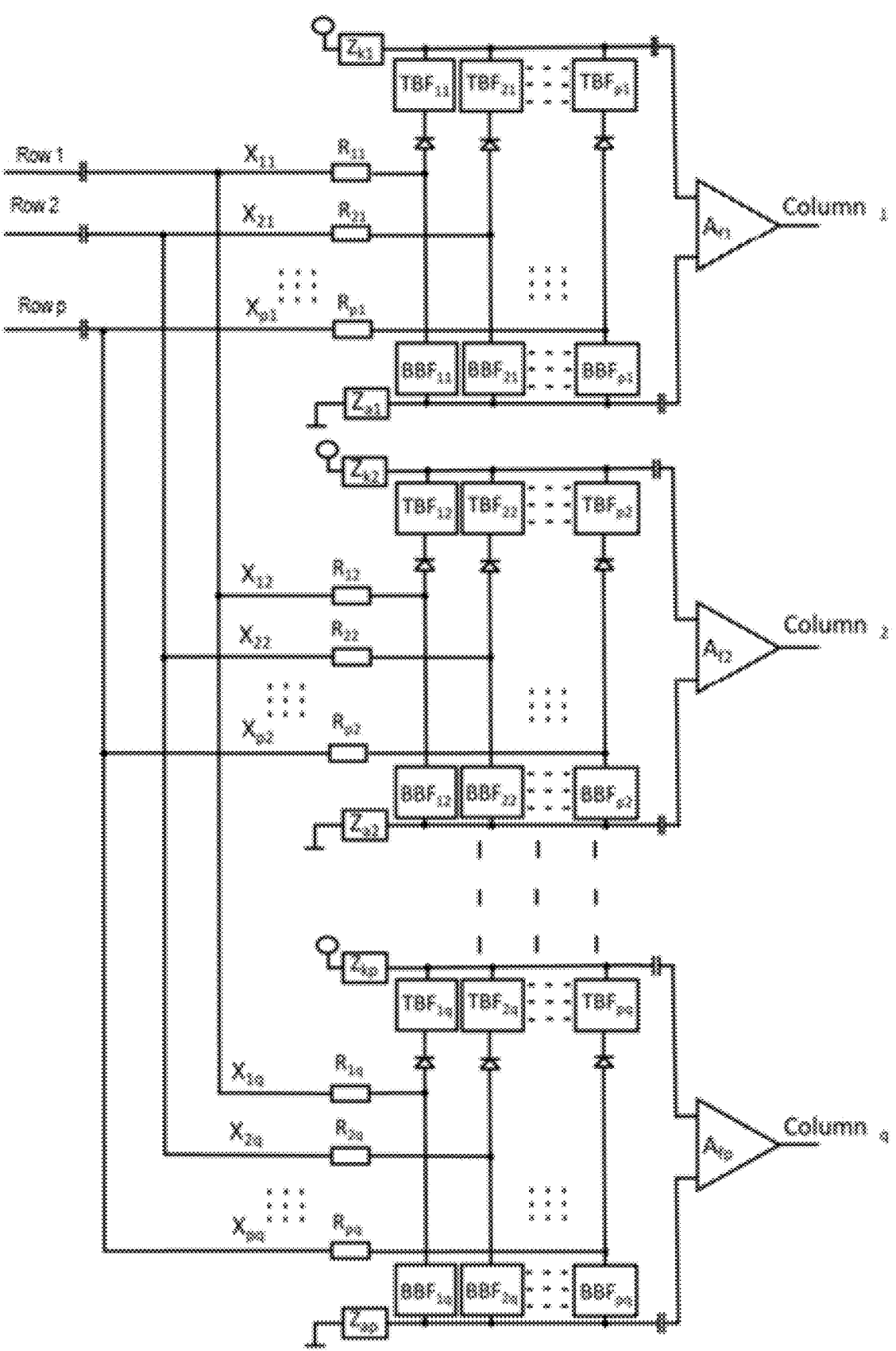
FIG. 12 shows the same particular scheme as FIG. 11, in which we apply a simplification of the sub-circuit of the CF filters in series, which allows us to reduce the number of components, leaving only one common capacitor for all the C-R filters. in series, and a resistor on each load output to the filter.

The readout network circuits of FIG. 11 or FIG. 12 are the result of the stacking of readout networks of a column and can have any of the networks described in the 7 previous embodiments as a lower level readout network. We can refer to any of these examples to know the specific details of each one. They could have, for example, 16 readout networks, each one having one column and 16 rows (p=16). This allows us to form a stacked readout network of 16 rows+16 columns. These 32 signs can be simultaneously read to know the impact positions anywhere in the detector, and an impact timestamp of each column.

The circuit in FIG. 12 is derived from that in FIG. 11, as a simplification, since all the C-R filters are linked in series at one of the terminals, that part of the circuit can be replaced by an equal number of equivalent filters created at starting from a common component (for example the capacitor C), after which the other components (for example all the resistors of the replaced filters) are derived by separate connections.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A readout network topology for positron emission tomography (PET) with time of flight (TOF) capabilities to extract position and time information in the area of gamma-ray detection, comprising:

a plurality of individual photodetectors arranged in a p×q matrix configuration on an electronic Printed Circuit Board (PCB) to conform a photodetector capable to process light arriving to a matrix area and providing information to determine spatial coordinates and a timing signal, each individual photodetector having an anodic terminal and a cathodic terminal;

a connection of all similar terminals of one of the two types of the photodetector terminals, either anodes or cathodes, to a Single Junction at the PCB, which further splits into two routes:

the first one of these routes connects the Single Junction, by a specific impedance, to a proper source polarity, wherein the proper source polarity is Vbias if the similar terminals to the Single Junction are the cathodes or GND if the similar terminals to the Single Junction are the anodes, and wherein the specific impedance:

is Za if the similar terminals are the anodes or Zk if the similar terminals are the cathodes, is working as part of a photodetector bias circuit, and has a resistance set to be less than 10% compared to a resistance of a remainder of the first route from the Single Junction to GND; and the second one of these routes is connected to a unified signal created at the Single Junction, into a fast amplifier, in order to obtain a single timing signal regarding the photodetector, no matter which of the plurality of individual photodetectors it comes from;

an individual connection of all other photodetector terminals, different from the similar terminals connected to the Single Junction, by two separate types of filtering circuits for each of the other photodetector terminals, the first type of filtering circuits connecting the individual photodetector terminals to the proper source polarity to complete the bias circuits for all individual photodetectors; and, the second type of filtering circuits function as output signal filters, to obtain individual current signals from each individual photodetector, representing a quantity of light captured by each individual photodetector in the matrix, giving rise to uncoupled $X_i$ signals.

2. The readout network topology according to claim 1, wherein the timing signal is a sum of all the cathodes at the Single Junction.

3. The readout network topology according to claim 1, wherein the timing signal is the sum of all the cathodes including routed delay lines at the Single Junction.

4. The readout network topology according to claim 1, wherein the timing signal is the sum, at the Single Junction, of all the anodes.

5. The readout network topology according to claim 1, wherein the timing signal is the result of a differential signal between a first Single Junction of all the cathodes of the individual photodetectors and a second Single Junction of all the anodes of the individual photodetectors connected to the second Single Junction via a filter.

6. The readout network topology according to claim 1, wherein the timing signal is the result of a differential signal between a first Single Junction of the anodes of all individual photodetectors and a second Single Junction of the cathodes of all individual photodetectors connected to the first Single Junction via a filter.

7. The readout network topology according to claim 1, wherein the timing signal is the result of the Single Junction of the cathodes of all individual photodetectors connected to the Single Junction via a filter.

8. The readout network topology according to claim 1, wherein the timing signal is the result of the Single Junction of the anodes of all individual photodetectors connected to the Single Junction via a filter.

9. The readout network topology according to claim 1, wherein the individual photodetectors are each a Silicon Photomultiplier (SiPM).

10. An imaging system, comprising:

a plurality of readout networks for positron emission tomography (PET), wherein each readout network has time of flight (TOF) capabilities to extract position and time information in the area of gamma-ray detection, each readout network further comprises:

a plurality of individual photodetectors arranged in a pxq matrix configuration on an electronic Printed Circuit Board (PCB) to conform a photodetector capable to process light arriving to a matrix area and providing information to determine spatial coordinates and a timing signal, each individual photodetector having an anodic terminal and a cathodic terminal;

a connection of all similar terminals of one of the two types of the photodetector, terminals, either anodes or cathodes, to a Single Junction at the PCB, which further splits into two routes:

the first one of these routes connects the Single Junction, by a specific impedance, to a proper source polarity, wherein the proper source polarity is Vbias if the similar terminals to the Single Junction are the cathodes or GND if the similar terminals to the Single Junction are the anodes, and wherein the specific impedance:

is Za if the similar terminals are the anodes or Zk if the similar terminals are the cathodes, is working as part of a photodetector bias circuit, and has a resistance set to be less than 10% compared to a resistance of a remainder of the first route from the Single Junction to GND; and the second one of these routes is connected to a unified signal created at the Single Junction, into a fast amplifier, in order to obtain a single timing signal regarding the photodetector, no matter which of the plurality of individual photodetectors it comes from;

an individual connection of all other photodetector terminals, different from the similar terminals connected to the Single Junction, by two separate types of filtering circuits for each of the other photodetector terminals, the first type of filtering circuits connecting the individual photodetector terminals to the proper source polarity to complete the bias circuits for all individual photodetectors; and, the second type of filtering circuits functioning as output signal filters, to obtain individual current signals from each individual photodetector, representing the quantity of light captured by each individual photodetector in the matrix, giving rise to uncoupled $X_i$ signals.

11. The imaging system according to claim 10, wherein the plurality of readout networks includes a number, q, of readout networks, each having a single column and a number, p, of rows, to define a higher level readout network topology with p rows and q columns.

12. The imaging system according to claim 11, wherein the timing signal obtained from each readout network is connected to a charge readout circuit in order to obtain energy and position information regarding the plurality of readout networks.

13. The imaging system according to claim 12, wherein the timing signal from each column is connected to a first charge readout circuit to obtain energy and position information with respect to the columns of the plurality of readout networks and the timing signal from each row is connected to a second charge readout circuit to obtain energy and position information with respect to the rows of the plurality of readout networks.

14. The imaging system according to claim 10, wherein the plurality of readout networks includes a number, p, of readout networks, each having a single row and a number of columns, q, to define a higher level readout network topology with p rows and q columns.

15. The imaging system according to claim 14, wherein the timing signal obtained from each readout network is connected to a charge readout circuit to obtain energy and position information with respect to the plurality of readout networks.

16. The imaging system according to claim 15, wherein the timing signal from each row is connected to a first charge readout circuit to obtain energy and position information with respect to the rows of the plurality of readout networks and the timing signal from each column is connected to a second charge readout circuit to obtain energy and position information with respect to the columns of the plurality of readout networks.

17. The imaging system according to claim 10 further comprising:

a scintillator crystal part facing the photodetector;

a housing to protect the imaging system from external light and mechanical stress; and an analog to digital conversion circuit capable of processing all positioning and energy signals obtained and transmitting these through a high-speed computer interface to be processed on the fly, or stored in a computer disk, to be later processed, as well as preserving the timing signal.

18. The imaging system of claim 10, further comprising at least one detector module, each detector module comprising at least one readout network; a mechanical gantry, having a symmetrical configuration, with the at least one detector module positioned around and facing a volume of detection, a coincidence processing electronic module capable to process the timing signals coming from the plurality of modules to provide proper matching among multiple combinations of the at least one detector module to effectively process as a single block, all signals related to any single PET event, no matter which module they come from, wherein the coincidence processing electronic module is further capable to digitize and transmit all the timing signals through a high-speed computer interface to be processed on the fly, or stored in a computer disk, to be later processed, including time of flight information of all detected events.

19. The imaging system according to claim 18, further comprising a software module capable of processing all the data stored in a computer or received in real time, to provide high-quality ToF-PET images, using any computer or digital interface.

20. A method for obtaining time and position information from the signals coming from a ToF-PET photodetector, in a detector module of a PET device, the method comprising the steps of:

arranging a scintillation crystal in a detector module;

arranging a readout network topology for positron emission tomography (PET) with time of flight (TOF) capabilities to extract position and time information in an area of gamma-ray detection, said readout network topology comprising:

a plurality of individual photodetectors arranged in a p×q matrix configuration on an electronic Printed Circuit Board (PCB) to conform a photodetector capable to process light arriving to a matrix area and providing information to determine spatial coordinates and a timing signal, each individual photodetector having an anodic terminal and a cathodic terminal;

a connection of all similar terminals of one of the two types of the photodetector terminals, either anodes or cathodes, to a Single Junction at the PCB, which further splits into two routes:

the first one of these routes connects the Single Junction, by a specific impedance, to a proper source polarity, wherein the proper source polarity is Vbias if the similar terminals to the Single Junction are the cathodes or GND if the similar terminals to the Single Junction are the anodes, and wherein the specific impedance:

is Za if the similar terminals are the anodes or Zk if the similar terminals are the cathodes, is working as part of a photodetector bias circuit, and has a resistance set to be less than 10% compared to a resistance of a remainder of the first route from the Single Junction to GND; and the second one of these routes is connected to a unified signal created at the Single Junction, into a fast amplifier, in order to obtain a single timing signal regarding the photodetector, no matter which of the plurality of individual photodetectors it comes from;

an individual connection of all other photodetector terminals, different from the similar terminals connected to the Single Junction, by two separate types of filtering circuits for each of the other photodetector terminals, the first type of filtering circuits connecting the individual photodetector terminals to the proper source polarity to complete the bias circuits for all individual photodetectors; and, the second type of filtering circuits function as output signal filters, to obtain individual current signals from each individual photodetector, representing a quantity of light captured by each individual photodetector in the matrix, giving rise to uncoupled $X_i$ signals;

receiving a gamma ray into the detector module and impinging the scintillation crystal;

creating a light beam from the gamma ray incident on the scintillation crystal which is emitted out from the scintillation crystal to the readout network topology;

converting the light beam into a distribution of electrical signals coming from the plurality of individual photodetectors, providing a first signal detected from any one of the plurality of individual photodetectors to a fast amplifier, the first signal corresponding to the instant of the arrival of the gamma ray to the scintillator crystal volume;

generating an output timing signal from the fast amplifier;

transmitting the electrical signals from each of the plurality of individual photodetectors via charge filters to provide uncoupled charge signal outputs compatible with readout electronic circuits used to extract position and energy of the gamma ray.

21. The method according to claim 20 that further comprises the steps of:

handling data from at least two detector modules;

providing information according to claim 15; and obtaining a plurality of ToF lines of response required to create a ToF-PET image.

* * * * *